US008845687B2

(12) United States Patent
Bonutti

(10) Patent No.: US 8,845,687 B2
(45) Date of Patent: Sep. 30, 2014

(54) ANCHOR FOR SECURING A SUTURE

(71) Applicant: Bonutti Skeletal Innovations LLC, Plano, TX (US)

(72) Inventor: Peter M. Bonutti, Effingham, IL (US)

(73) Assignee: Bonutti Skeletal Innovations LLC, Plano, TX (US)

( * ) Notice: Subject to any disclaimer, the term of this patent is extended or adjusted under 35 U.S.C. 154(b) by 0 days.

(21) Appl. No.: 14/029,076

(22) Filed: Sep. 17, 2013

(65) Prior Publication Data

US 2014/0018853 A1    Jan. 16, 2014

Related U.S. Application Data

(60) Continuation of application No. 11/230,020, filed on Sep. 19, 2005, which is a continuation of application No. 10/442,353, filed on May 21, 2003, now Pat. No. 6,955,683, which is a continuation of application No. 09/703,058, filed on Oct. 31, 2000, now Pat. No. 6,572,635, which is a continuation of application No. 09/378,190, filed on Aug. 20, 1999, now Pat. No. 6,152,949, which is a continuation of application No. 08/964,167, filed on Nov. 4, 1997, now Pat. No. 5,980,559, which is a division of application No. 08/699,553, filed on Aug. 19, 1996, now Pat. No. 5,718,717.

(51) Int. Cl.
*A61B 17/04* (2006.01)

(52) U.S. Cl.
CPC ..... *A61B 17/0401* (2013.01); *A61B 2017/0403* (2013.01); *A61B 2017/0414* (2013.01); *A61B 2017/0427* (2013.01); *A61B 2017/0409* (2013.01); *A61B 2017/0417* (2013.01); *A61B 2017/0458* (2013.01); *A61B 2017/0445* (2013.01); *A61B 2017/047* (2013.01); *A61B 2017/0412* (2013.01)
USPC ........................................................ 606/232

(58) Field of Classification Search
CPC ................... A61B 17/0401; A61B 2017/0414; A61B 2017/0412; A61B 2017/042; A61B 2017/0427; A61B 2017/0446
USPC .......................................... 606/232, 65, 304
See application file for complete search history.

(56) References Cited

U.S. PATENT DOCUMENTS

| 157,343 A | 12/1874 | Molesworth |
| 319,296 A | 6/1885 | Molesworth |

(Continued)

FOREIGN PATENT DOCUMENTS

| CA | 1312518 C | 1/1993 |
| CA | 2641580 | 8/2007 |

(Continued)

OTHER PUBLICATIONS

U.S. Appl. No. 13/221,043, filed Jun. 2011, Bonutti.

(Continued)

*Primary Examiner* — Katherine Dowe
(74) *Attorney, Agent, or Firm* — Martin & Ferraro, LLP

(57) ABSTRACT

An anchor, formed of at least two different materials, for securing a suture relative to bone. The anchor includes a generally cylindrical body portion having a leading end configured to facilitate insertion of the body portion into the bone; a passage which is oriented transverse to the longitudinal axis of the body portion and proximate the leading end of the body portion; and bone engaging projections to secure the anchor in the bone.

13 Claims, 5 Drawing Sheets

(56) References Cited

U.S. PATENT DOCUMENTS

| | | |
|---|---|---|
| 668,878 A | 2/1901 | Jensen |
| 668,879 A | 2/1901 | Miller |
| 673,783 A | 5/1901 | Peters |
| 702,789 A | 6/1902 | Gibson |
| 832,201 A | 10/1906 | Kistler |
| 862,712 A | 8/1907 | Collins |
| 1,213,005 A | 1/1917 | Pillsbury |
| 1,433,031 A | 10/1922 | Henri |
| 1,725,670 A | 8/1929 | William |
| 1,863,057 A | 6/1932 | Innes |
| 1,870,942 A | 8/1932 | Beatty |
| 2,121,193 A | 12/1932 | Hanicke |
| 1,909,967 A | 5/1933 | Jones |
| 1,959,615 A | 5/1934 | Derrah |
| 2,187,852 A | 8/1936 | Friddle |
| 2,178,840 A | 11/1936 | Lorenian |
| 2,199,025 A | 4/1940 | Conn |
| 2,235,419 A | 3/1941 | Callahan |
| 2,248,054 A | 7/1941 | Becker |
| 2,270,188 A | 1/1942 | Longfellow |
| 2,433,815 A | 12/1947 | Nicephore et al. |
| 2,518,276 A | 8/1950 | Brawand |
| 2,526,662 A | 10/1950 | Hipps et al. |
| 2,557,669 A | 6/1951 | Lloyd |
| 2,566,499 A | 9/1951 | Richter |
| 2,589,720 A | 3/1952 | Marl |
| 2,621,145 A | 12/1952 | Sano |
| 2,621,653 A | 12/1952 | Briggs |
| 2,642,874 A | 6/1953 | Keeling |
| 2,687,719 A | 8/1954 | William |
| 2,701,559 A | 2/1955 | Cooper |
| 2,724,326 A | 11/1955 | Long |
| 2,725,053 A | 11/1955 | Bambara |
| 2,830,587 A | 4/1958 | Everett |
| 2,854,983 A | 10/1958 | Baskin |
| 2,936,760 A | 5/1960 | Gants |
| 2,955,530 A | 10/1960 | Nilo |
| 3,039,468 A | 6/1962 | Price |
| 3,048,522 A | 8/1962 | Velley |
| 3,081,773 A | 3/1963 | Boyd |
| 3,108,357 A | 10/1963 | Liebig |
| 3,108,595 A | 10/1963 | Overment |
| 3,204,635 A | 9/1965 | Voss et al. |
| 3,229,006 A | 1/1966 | Egon |
| 3,253,594 A | 5/1966 | Matthews et al. |
| 3,347,234 A | 10/1967 | Voss |
| 3,367,809 A | 2/1968 | Soloff |
| 3,391,690 A | 7/1968 | Armao |
| 3,397,699 A | 8/1968 | Kohl |
| 3,417,745 A | 12/1968 | Emanuel |
| 3,459,175 A | 8/1969 | Miller |
| 3,469,003 A | 9/1969 | Hardy |
| 3,477,429 A | 11/1969 | Sampson |
| 3,495,586 A | 2/1970 | Regenbogen |
| 3,513,848 A | 5/1970 | Winston et al. |
| 3,514,791 A | 6/1970 | Sparks |
| 3,517,128 A | 6/1970 | Hines |
| 3,518,993 A | 7/1970 | Blake |
| 3,554,192 A | 1/1971 | Isberner |
| 3,557,794 A | 1/1971 | Patten |
| 3,577,991 A | 5/1971 | Wilkinson |
| 3,593,709 A | 7/1971 | Halloran |
| 3,596,292 A | 8/1971 | Erb et al. |
| 3,608,539 A | 9/1971 | Miller |
| 3,613,497 A | 10/1971 | Heldermann |
| 3,620,218 A | 11/1971 | Schmitt et al. |
| 3,624,747 A | 11/1971 | McKnight et al. |
| 3,625,220 A | 12/1971 | Engelsher |
| 3,626,949 A | 12/1971 | Shute |
| 3,635,223 A | 1/1972 | Klieman |
| 3,648,705 A | 3/1972 | Lary |
| 3,653,388 A | 4/1972 | Tenckhoff |
| 3,656,476 A | 4/1972 | Swinney |
| 3,657,056 A | 4/1972 | Winston et al. |
| 3,670,732 A | 6/1972 | Robinson |
| 3,678,980 A | 7/1972 | Gutshall |
| 3,698,017 A | 10/1972 | Scales et al. |
| 3,709,218 A | 1/1973 | Halloran |
| 3,711,347 A | 1/1973 | Wagner et al. |
| 3,716,051 A | 2/1973 | Fischer |
| 3,721,244 A | 3/1973 | Elmaleh |
| 3,739,773 A | 6/1973 | Schmitt et al. |
| 3,750,652 A | 8/1973 | Sherwin |
| 3,760,808 A | 9/1973 | Bleuer |
| 3,769,980 A | 11/1973 | Karman |
| 3,774,244 A | 11/1973 | Walker |
| 3,774,596 A | 11/1973 | Cook |
| 3,779,239 A | 12/1973 | Fischer et al. |
| 3,788,318 A | 1/1974 | Kim et al. |
| 3,789,852 A | 2/1974 | Kim et al. |
| 3,800,788 A | 4/1974 | White |
| 3,802,438 A | 4/1974 | Wolvek |
| 3,804,089 A | 4/1974 | Bridgman |
| 3,807,393 A | 4/1974 | McDonald |
| 3,807,394 A | 4/1974 | Attenborough |
| 3,809,075 A | 5/1974 | Matles |
| 3,811,449 A | 5/1974 | Gravlee et al. |
| 3,812,855 A | 5/1974 | Banko |
| 3,825,010 A | 7/1974 | McDonald |
| 3,833,003 A | 9/1974 | Taricco |
| 3,835,849 A | 9/1974 | McGuire |
| 3,841,304 A | 10/1974 | Jones |
| 3,842,824 A | 10/1974 | Neufeld |
| 3,845,772 A | 11/1974 | Smith |
| 3,850,172 A | 11/1974 | Cazalis |
| 3,850,720 A | 11/1974 | Collins |
| 3,852,830 A | 12/1974 | Marmor |
| 3,857,396 A | 12/1974 | Hardwick |
| 3,863,639 A | 2/1975 | Kleaveland |
| 3,867,932 A | 2/1975 | Huene |
| 3,869,731 A | 3/1975 | Waugh et al. |
| 3,874,264 A | 4/1975 | Polos |
| 3,875,652 A | 4/1975 | Arnold |
| 3,875,946 A | 4/1975 | Duncan |
| 3,882,852 A | 5/1975 | Sinnreich |
| 3,889,686 A | 6/1975 | Duturbure et al. |
| 3,894,530 A | 7/1975 | Dardik et al. |
| 3,898,992 A | 8/1975 | Balamuth |
| 3,903,549 A | 9/1975 | Deyerle |
| 3,911,923 A | 10/1975 | Yoon |
| 3,915,171 A | 10/1975 | Shermeta |
| 3,918,442 A | 11/1975 | Nikolaev et al. |
| 3,920,022 A | 11/1975 | Pastor |
| 3,939,835 A | 2/1976 | Bridgman |
| 3,945,375 A | 3/1976 | Banko |
| 3,960,143 A | 6/1976 | Terada |
| 3,961,632 A | 6/1976 | Moossun |
| 3,967,625 A | 7/1976 | Yoon |
| 3,968,800 A | 7/1976 | Vilasi |
| 3,970,089 A | 7/1976 | Saice |
| 3,973,277 A | 8/1976 | Semple et al. |
| 3,976,079 A | 8/1976 | Samuels et al. |
| 3,989,049 A | 11/1976 | Yoon |
| 3,991,426 A | 11/1976 | Flom et al. |
| 3,994,287 A | 11/1976 | Turp et al. |
| 4,000,525 A | 1/1977 | Klawitter et al. |
| 4,022,216 A | 5/1977 | Stevens |
| 4,023,559 A | 5/1977 | Gaskell |
| 4,040,413 A | 8/1977 | Ohshiro |
| 4,053,953 A | 10/1977 | Flom et al. |
| 4,055,862 A | 11/1977 | Farling |
| 4,064,566 A | 12/1977 | Fletcher et al. |
| 4,077,412 A | 3/1978 | Moossun |
| 4,081,866 A | 4/1978 | Upshaw et al. |
| 4,083,369 A | 4/1978 | Sinnreich |
| 4,085,466 A | 4/1978 | Goodfellow et al. |
| 4,085,743 A | 4/1978 | Yoon |
| 4,089,071 A | 5/1978 | Kainberz et al. |
| 4,092,113 A | 5/1978 | Hardy |
| 4,103,680 A | 8/1978 | Yoon |
| RE29,757 E | 9/1978 | Helfet |
| 4,122,605 A | 10/1978 | Hirabay et al. |
| 4,142,517 A | 3/1979 | Contreras et al. |
| 4,148,307 A | 4/1979 | Utsugi |

(56) References Cited

U.S. PATENT DOCUMENTS

| | | | |
|---|---|---|---|
| 4,156,574 | A | 5/1979 | Boben |
| 4,164,794 | A | 8/1979 | Spector et al. |
| 4,169,470 | A | 10/1979 | Ender et al. |
| 4,171,544 | A | 10/1979 | Hench et al. |
| 4,177,814 | A | 12/1979 | Knepshield et al. |
| 4,183,102 | A | 1/1980 | Guiset |
| 4,186,448 | A | 2/1980 | Brekke |
| 4,191,747 | A | 3/1980 | Scheicher |
| 4,198,981 | A | 4/1980 | Sinnreich |
| 4,199,864 | A | 4/1980 | Ashman |
| 4,200,939 | A | 5/1980 | Oser |
| 4,203,444 | A | 5/1980 | Bonnell et al. |
| 4,209,012 | A | 6/1980 | Smucker |
| 4,209,861 | A | 7/1980 | Borzone et al. |
| 4,210,148 | A | 7/1980 | Stivala |
| 4,210,580 | A | 7/1980 | Amrani |
| 4,213,209 | A | 7/1980 | Insall et al. |
| 4,213,816 | A | 7/1980 | Morris |
| 4,224,696 | A | 9/1980 | Murray et al. |
| 4,224,929 | A | 9/1980 | Furihata |
| 4,228,802 | A | 10/1980 | Trott |
| 4,230,119 | A | 10/1980 | Blum |
| 4,235,233 | A | 11/1980 | Mouwen |
| 4,235,238 | A | 11/1980 | Ogiu et al. |
| 4,240,433 | A | 12/1980 | Bordow |
| 4,243,048 | A | 1/1981 | Griffin |
| 4,244,370 | A | 1/1981 | Furlow et al. |
| 4,257,411 | A | 3/1981 | Cho |
| 4,263,900 | A | 4/1981 | Nicholson |
| 4,265,231 | A | 5/1981 | Scheller, Jr. et al. |
| 4,265,848 | A | 5/1981 | Ruesch |
| 4,274,414 | A | 6/1981 | Johnson et al. |
| 4,281,649 | A | 8/1981 | Derweduwen |
| 4,291,698 | A | 9/1981 | Fuchs |
| 4,295,464 | A | 10/1981 | Shihata |
| 4,298,002 | A | 11/1981 | Ronel et al. |
| 4,298,992 | A | 11/1981 | Burstein et al. |
| 4,298,998 | A | 11/1981 | Naficy |
| 4,299,224 | A | 11/1981 | Noiles |
| 4,299,227 | A | 11/1981 | Lincoff |
| 4,304,178 | A | 12/1981 | Haeberle |
| 4,309,488 | A | 1/1982 | Heide et al. |
| 4,311,145 | A | 1/1982 | Esty et al. |
| 4,312,353 | A | 1/1982 | Shahbabian |
| 4,320,762 | A | 3/1982 | Bentov |
| 4,344,193 | A | 8/1982 | Kenny |
| 4,349,029 | A | 9/1982 | Mott |
| 4,349,921 | A | 9/1982 | Kuntz |
| 4,351,069 | A | 9/1982 | Ballintyn et al. |
| 4,352,883 | A | 10/1982 | Lim |
| 4,357,940 | A | 11/1982 | Muller |
| 4,364,381 | A | 12/1982 | Sher et al. |
| 4,365,356 | A | 12/1982 | Broemer et al. |
| 4,369,768 | A | 1/1983 | Vukovic |
| 4,373,217 | A | 2/1983 | Draenert |
| 4,373,709 | A | 2/1983 | Whitt |
| 4,374,523 | A | 2/1983 | Yoon |
| 4,385,404 | A | 5/1983 | Sully et al. |
| 4,388,921 | A | 6/1983 | Sutter et al. |
| 4,391,909 | A | 7/1983 | Lim |
| 4,395,798 | A | 8/1983 | Mc Vey |
| 4,400,833 | A | 8/1983 | Kurland |
| 4,407,273 | A | 10/1983 | Ouchi |
| 4,409,974 | A | 10/1983 | Freedland |
| 4,414,166 | A | 11/1983 | Charlson et al. |
| 4,421,112 | A | 12/1983 | Mains et al. |
| 4,430,760 | A | 2/1984 | Smestad |
| 4,434,797 | A | 3/1984 | Silander |
| 4,437,191 | A | 3/1984 | Van der Zat et al. |
| 4,437,362 | A | 3/1984 | Hurst |
| 4,442,655 | A | 4/1984 | Stroetmann et al. |
| 4,444,180 | A | 4/1984 | Schneider et al. |
| 4,445,509 | A | 5/1984 | Auth |
| 4,447,227 | A | 5/1984 | Kotsanis |
| 4,448,194 | A | 5/1984 | DiGiovanni et al. |
| 4,450,591 | A | 5/1984 | Rappaport |
| 4,453,421 | A | 6/1984 | Umano |
| 4,453,539 | A | 6/1984 | Raftopoulos et al. |
| 4,456,005 | A | 6/1984 | Lichty |
| 4,457,302 | A | 7/1984 | Caspari et al. |
| 4,461,281 | A | 7/1984 | Carson |
| 4,466,429 | A | 8/1984 | Loscher et al. |
| 4,466,888 | A | 8/1984 | Verkaart |
| 4,472,840 | A | 9/1984 | Jefferies |
| 4,474,177 | A | 10/1984 | Whiteside |
| 4,484,579 | A | 11/1984 | Meno et al. |
| 4,485,096 | A | 11/1984 | Bell |
| 4,487,203 | A | 12/1984 | Androphy |
| 4,493,317 | A | 1/1985 | Klaue |
| 4,495,664 | A | 1/1985 | Bianquaert |
| 4,501,031 | A | 2/1985 | McDaniel et al. |
| 4,501,266 | A | 2/1985 | McDaniel |
| 4,501,269 | A | 2/1985 | Bagby |
| 4,502,159 | A | 3/1985 | Woodroof et al. |
| 4,502,161 | A | 3/1985 | Wall |
| 4,504,268 | A | 3/1985 | Herlitze |
| 4,505,274 | A | 3/1985 | Speelman |
| 4,506,681 | A | 3/1985 | Mundell |
| 4,509,518 | A | 4/1985 | McGarry et al. |
| 4,514,125 | A | 4/1985 | Stol |
| 4,516,276 | A | 5/1985 | Mittelmeier et al. |
| 4,526,173 | A | 7/1985 | Sheehan |
| 4,532,926 | A | 8/1985 | O'Halla |
| 4,535,757 | A | 8/1985 | Webster |
| 4,535,772 | A | 8/1985 | Sheehan |
| 4,540,404 | A | 9/1985 | Wolvek |
| 4,541,423 | A | 9/1985 | Barber |
| 4,545,374 | A | 10/1985 | Jacobson |
| 4,545,375 | A | 10/1985 | Cline |
| 4,547,327 | A | 10/1985 | Bruins et al. |
| 4,551,135 | A | 11/1985 | Gorman et al. |
| 4,553,272 | A | 11/1985 | Mears |
| 4,554,686 | A | 11/1985 | Baker |
| 4,555,242 | A | 11/1985 | Saudagar |
| 4,556,059 | A | 12/1985 | Adamson, Jr. |
| 4,556,350 | A | 12/1985 | Bernhardt et al. |
| 4,556,391 | A | 12/1985 | Tardivel et al. |
| 4,562,598 | A | 1/1986 | Kranz |
| 4,565,192 | A | 1/1986 | Shapiro |
| 4,566,138 | A | 1/1986 | Lewis et al. |
| 4,572,186 | A | 2/1986 | Gould et al. |
| 4,573,448 | A | 3/1986 | Kambin |
| 4,574,794 | A | 3/1986 | Cooke et al. |
| 4,575,371 | A | 3/1986 | Nordqvist et al. |
| 4,584,722 | A | 4/1986 | Levy |
| 4,585,000 | A | 4/1986 | Hershenson |
| 4,589,414 | A | 5/1986 | Yoshida et al. |
| 4,589,686 | A | 5/1986 | McGrew |
| 4,589,868 | A | 5/1986 | Dretler |
| 4,590,928 | A | 5/1986 | Hunt et al. |
| 4,597,379 | A | 7/1986 | Kihn et al. |
| 4,599,085 | A | 7/1986 | Riess et al. |
| 4,601,893 | A | 7/1986 | Cardinal |
| 4,603,694 | A | 8/1986 | Wheeler |
| 4,606,335 | A | 8/1986 | Wedeen |
| 4,608,052 | A | 8/1986 | Van Kampen et al. |
| 4,608,965 | A | 9/1986 | Anspach, Jr. et al. |
| 4,610,662 | A | 9/1986 | Weikl et al. |
| 4,611,593 | A | 9/1986 | Fogarty et al. |
| 4,615,717 | A | 10/1986 | Neubauer et al. |
| 4,619,391 | A | 10/1986 | Sharkany et al. |
| 4,621,640 | A | 11/1986 | Mulhollan et al. |
| 4,623,553 | A | 11/1986 | Ries et al. |
| 4,624,254 | A | 11/1986 | McGarry et al. |
| 4,630,609 | A | 12/1986 | Chin |
| 4,632,101 | A | 12/1986 | Freedland |
| 4,641,648 | A | 2/1987 | Shapiro |
| 4,642,117 | A | 2/1987 | Nguyen et al. |
| 4,642,120 | A | 2/1987 | Nevo et al. |
| 4,645,503 | A | 2/1987 | Lin et al. |
| 4,646,736 | A | 3/1987 | Auth |
| 4,646,738 | A | 3/1987 | Trott |
| 4,649,918 | A | 3/1987 | Pegg et al. |
| 4,651,717 | A | 3/1987 | Jakubczak |

(56) References Cited

U.S. PATENT DOCUMENTS

| | | |
|---|---|---|
| 4,651,752 A | 3/1987 | Fuerst |
| 4,654,464 A | 3/1987 | Mittelmeier et al. |
| 4,657,460 A | 4/1987 | Bien |
| 4,657,548 A | 4/1987 | Nichols |
| 4,659,268 A | 4/1987 | Del Mundo et al. |
| 4,662,063 A | 5/1987 | Collins et al. |
| 4,662,068 A | 5/1987 | Polonsky |
| 4,662,372 A | 5/1987 | Sharkany et al. |
| 4,662,887 A | 5/1987 | Turner et al. |
| 4,669,473 A | 6/1987 | Richards et al. |
| 4,678,470 A | 7/1987 | Nashef et al. |
| 4,681,106 A | 7/1987 | Kensey et al. |
| 4,681,107 A | 7/1987 | Kees, Jr. |
| 4,682,598 A | 7/1987 | Beraha |
| 4,685,458 A | 8/1987 | Leckrone |
| 4,685,460 A | 8/1987 | Thornton |
| 4,691,741 A | 9/1987 | Affa et al. |
| 4,696,667 A | 9/1987 | Masch |
| 4,705,040 A | 11/1987 | Mueller et al. |
| 4,706,659 A | 11/1987 | Matthews et al. |
| 4,706,670 A | 11/1987 | Andersen et al. |
| 4,708,139 A | 11/1987 | Dunbar, IV |
| 4,711,233 A | 12/1987 | Brown |
| 4,712,542 A | 12/1987 | Daniel |
| 4,713,076 A | 12/1987 | Draenert |
| 4,713,077 A | 12/1987 | Small |
| 4,714,074 A | 12/1987 | Rey et al. |
| 4,716,893 A | 1/1988 | Fischer et al. |
| 4,716,901 A | 1/1988 | Jackson et al. |
| 4,718,909 A | 1/1988 | Brown |
| 4,718,916 A | 1/1988 | Morscher |
| 4,719,908 A | 1/1988 | Averill et al. |
| 4,721,096 A | 1/1988 | Naughton et al. |
| 4,721,103 A | 1/1988 | Freedland |
| 4,721,104 A | 1/1988 | Kaufman et al. |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble et al. |
| 4,739,751 A | 4/1988 | Sapega et al. |
| 4,741,330 A | 5/1988 | Hayhurst |
| 4,743,229 A | 5/1988 | Chu |
| 4,743,259 A | 5/1988 | Bolander et al. |
| 4,744,364 A | 5/1988 | Kensey |
| 4,747,405 A | 5/1988 | Leckrone |
| 4,749,585 A | 6/1988 | Greco et al. |
| 4,750,488 A | 6/1988 | Wuchinich et al. |
| 4,750,492 A | 6/1988 | Jacobs |
| 4,751,922 A | 6/1988 | DiPietropolo |
| 4,755,184 A | 7/1988 | Silverberg |
| 4,759,350 A | 7/1988 | Dunn et al. |
| 4,768,507 A | 9/1988 | Fischell et al. |
| 4,772,286 A | 9/1988 | Goble et al. |
| 4,776,328 A | 10/1988 | Frey et al. |
| 4,776,738 A | 10/1988 | Winston |
| 4,776,851 A | 10/1988 | Bruchman et al. |
| 4,779,611 A | 10/1988 | Grooters et al. |
| 4,781,182 A | 11/1988 | Purnell et al. |
| 4,781,681 A | 11/1988 | Sharrow et al. |
| 4,781,922 A | 11/1988 | Bone |
| 4,784,133 A | 11/1988 | Mackin |
| 4,789,663 A | 12/1988 | Wallace et al. |
| 4,790,303 A | 12/1988 | Steffee |
| 4,790,819 A | 12/1988 | Li et al. |
| 4,792,336 A | 12/1988 | Hiavacek et al. |
| 4,793,359 A | 12/1988 | Sharrow |
| 4,794,854 A | 1/1989 | Swaim |
| 4,795,467 A | 1/1989 | Piez et al. |
| 4,796,629 A | 1/1989 | Grayzel |
| 4,798,205 A | 1/1989 | Bonomo et al. |
| 4,798,213 A | 1/1989 | Doppelt |
| 4,800,901 A | 1/1989 | Rosenberg |
| 4,801,299 A | 1/1989 | Brendel et al. |
| 4,802,479 A | 2/1989 | Haber et al. |
| 4,817,591 A | 4/1989 | Klause |
| 4,817,602 A | 4/1989 | Beraha |
| 4,822,224 A | 4/1989 | Carl et al. |
| 4,823,794 A | 4/1989 | Pierce |
| 4,825,857 A | 5/1989 | Kenna |
| 4,828,563 A | 5/1989 | Mueller et al. |
| 4,832,025 A | 5/1989 | Coates |
| 4,832,026 A | 5/1989 | Jones |
| 4,832,683 A | 5/1989 | Idemoto et al. |
| 4,834,752 A | 5/1989 | Van Kampen |
| 4,834,757 A | 5/1989 | Brantigan |
| 4,841,960 A | 6/1989 | Garner |
| 4,842,517 A | 6/1989 | Kawahara et al. |
| 4,843,112 A | 6/1989 | Gerhart |
| 4,844,064 A | 7/1989 | Thimsen et al. |
| 4,846,791 A | 7/1989 | Hattler et al. |
| 4,846,812 A | 7/1989 | Walker et al. |
| 4,846,835 A | 7/1989 | Grande |
| 4,857,045 A | 8/1989 | Rydell |
| 4,861,334 A | 8/1989 | Nawaz |
| 4,862,874 A | 9/1989 | Kellner |
| 4,862,882 A | 9/1989 | Venturi et al. |
| 4,862,974 A | 9/1989 | Warren et al. |
| 4,863,472 A | 9/1989 | Tormala et al. |
| 4,867,157 A | 9/1989 | McGurk-Burleson et al. |
| 4,869,242 A | 9/1989 | Galluzzo |
| 4,870,957 A | 10/1989 | Goble et al. |
| 4,875,468 A | 10/1989 | Krauter et al. |
| 4,877,020 A | 10/1989 | Vich |
| 4,880,429 A | 11/1989 | Stone |
| 4,883,048 A | 11/1989 | Purnell et al. |
| 4,883,666 A | 11/1989 | Sabel et al. |
| 4,888,022 A | 12/1989 | Huebsch |
| 4,890,612 A | 1/1990 | Kensey |
| 4,892,552 A | 1/1990 | Ainsworth et al. |
| 4,895,148 A | 1/1990 | Bays et al. |
| 4,898,156 A | 2/1990 | Gatturna et al. |
| 4,899,729 A | 2/1990 | Gill et al. |
| 4,899,743 A | 2/1990 | Nicholson et al. |
| 4,899,744 A | 2/1990 | Fujitsuka et al. |
| 4,901,721 A | 2/1990 | Hakki |
| 4,902,296 A | 2/1990 | Bolander et al. |
| 4,904,259 A | 2/1990 | Itay |
| 4,904,261 A | 2/1990 | Dove |
| 4,909,789 A | 3/1990 | Taguchi |
| 4,911,721 A | 3/1990 | Aendergaten et al. |
| 4,919,667 A | 4/1990 | Richmond |
| 4,921,478 A | 5/1990 | Solano et al. |
| 4,921,479 A | 5/1990 | Grayzel |
| 4,922,897 A | 5/1990 | Sapega et al. |
| 4,923,464 A | 5/1990 | Dipisa, Jr. |
| 4,924,865 A | 5/1990 | Bays et al. |
| 4,924,866 A | 5/1990 | Yoon |
| 4,927,412 A | 5/1990 | Menasche |
| 4,927,421 A | 5/1990 | Goble et al. |
| 4,932,956 A | 6/1990 | Reddy et al. |
| 4,932,959 A | 6/1990 | Horzewski et al. |
| 4,932,960 A | 6/1990 | Green et al. |
| 4,932,973 A | 6/1990 | Gendler |
| 4,935,023 A | 6/1990 | Whiteside et al. |
| 4,935,028 A | 6/1990 | Drews |
| 4,936,848 A | 6/1990 | Bagby |
| 4,936,852 A | 6/1990 | Kent et al. |
| 4,944,760 A | 7/1990 | Kenna |
| 4,945,625 A | 8/1990 | Winston |
| 4,945,896 A | 8/1990 | Gade |
| 4,946,468 A | 8/1990 | Li |
| 4,950,296 A | 8/1990 | McIntyre |
| 4,950,298 A | 8/1990 | Gustilo et al. |
| 4,952,213 A | 8/1990 | Bowman et al. |
| 4,954,126 A | 9/1990 | Wallsten |
| 4,955,910 A | 9/1990 | Bolesky |
| 4,957,498 A | 9/1990 | Caspari et al. |
| 4,961,740 A | 10/1990 | Ray et al. |
| 4,961,741 A | 10/1990 | Hayhurst |
| 4,961,954 A | 10/1990 | Goldberg et al. |
| 4,963,151 A | 10/1990 | Ducheyne et al. |
| 4,963,489 A | 10/1990 | Naughton et al. |
| 4,964,862 A | 10/1990 | Arms |
| 4,964,865 A | 10/1990 | Burkhead et al. |

(56) References Cited

U.S. PATENT DOCUMENTS

| | | |
|---|---|---|
| 4,966,583 A | 10/1990 | Debbas |
| 4,968,298 A | 11/1990 | Michelson |
| 4,968,315 A | 11/1990 | Gatturna |
| 4,969,888 A | 11/1990 | Scholten et al. |
| 4,969,892 A | 11/1990 | Burton et al. |
| 4,969,895 A | 11/1990 | McLeod et al. |
| 4,979,949 A | 12/1990 | Matsen, III et al. |
| 4,979,957 A | 12/1990 | Hodorek |
| 4,983,179 A | 1/1991 | Sjostrom |
| 4,984,563 A | 1/1991 | Renaud |
| 4,984,564 A | 1/1991 | Yuen |
| 4,985,038 A | 1/1991 | Lyell |
| 4,990,161 A | 2/1991 | Kampner |
| 4,994,047 A | 2/1991 | Walker et al. |
| 4,994,067 A | 2/1991 | Summers |
| 4,994,071 A | 2/1991 | MacGregor |
| 4,995,868 A | 2/1991 | Brazier |
| 4,997,445 A | 3/1991 | Hodorek |
| 4,998,539 A | 3/1991 | Delsanti |
| 5,002,550 A | 3/1991 | Li |
| 5,002,557 A | 3/1991 | Hasson |
| 5,002,563 A | 3/1991 | Pyka et al. |
| 5,007,912 A | 4/1991 | Albrektsson et al. |
| 5,009,652 A | 4/1991 | Morgan et al. |
| 5,009,662 A | 4/1991 | Wallace et al. |
| 5,009,663 A | 4/1991 | Broome |
| 5,009,664 A | 4/1991 | Sievers |
| 5,013,316 A | 5/1991 | Goble et al. |
| 5,015,247 A | 5/1991 | Michelson |
| 5,015,255 A | 5/1991 | Kuslich |
| 5,019,090 A | 5/1991 | Pinchuk |
| 5,019,104 A | 5/1991 | Whiteside et al. |
| 5,021,056 A | 6/1991 | Hofmann et al. |
| 5,021,059 A | 6/1991 | Kensey et al. |
| 5,026,373 A | 6/1991 | Ray et al. |
| 5,027,827 A | 7/1991 | Cody et al. |
| 5,032,132 A | 7/1991 | Matsen, III et al. |
| 5,035,699 A | 7/1991 | Coates |
| 5,035,713 A | 7/1991 | Friis |
| 5,037,404 A | 8/1991 | Gold et al. |
| 5,037,422 A | 8/1991 | Hayhurst et al. |
| 5,037,423 A | 8/1991 | Kenna |
| 5,041,093 A | 8/1991 | Chu |
| 5,041,114 A | 8/1991 | Chapman et al. |
| 5,041,125 A | 8/1991 | Montano |
| 5,041,129 A | 8/1991 | Hayhurst et al. |
| 5,042,976 A | 8/1991 | Ishitsu et al. |
| 5,046,513 A | 9/1991 | Gatturna et al. |
| 5,047,055 A | 9/1991 | Bao et al. |
| 5,051,049 A | 9/1991 | Wills |
| 5,053,009 A | 10/1991 | Herzberg |
| 5,053,039 A | 10/1991 | Hofmann et al. |
| 5,053,046 A | 10/1991 | Janese |
| 5,053,047 A | 10/1991 | Yoon |
| 5,059,193 A | 10/1991 | Kuslich |
| 5,059,206 A | 10/1991 | Winters |
| 5,060,678 A | 10/1991 | Bauman et al. |
| 5,061,274 A | 10/1991 | Kensey |
| 5,061,281 A | 10/1991 | Mares et al. |
| 5,061,286 A | 10/1991 | Lyle |
| 5,062,843 A | 11/1991 | Mahony |
| 5,069,674 A | 12/1991 | Fearnot et al. |
| 5,071,411 A | 12/1991 | Hillstead |
| 5,073,373 A | 12/1991 | O'Leary et al. |
| 5,078,731 A | 1/1992 | Hayhurst |
| 5,078,744 A | 1/1992 | Chvapil |
| 5,078,745 A | 1/1992 | Rhenter et al. |
| 5,082,670 A | 1/1992 | Gage et al. |
| 5,084,050 A | 1/1992 | Draenert |
| 5,084,051 A | 1/1992 | Tormala et al. |
| 5,085,660 A | 2/1992 | Lin |
| 5,085,661 A | 2/1992 | Moss |
| 5,092,348 A | 3/1992 | Dubrul et al. |
| 5,098,433 A | 3/1992 | Freedland |
| 5,098,434 A | 3/1992 | Serbousek |
| 5,098,436 A | 3/1992 | Ferrante et al. |
| 5,098,437 A | 3/1992 | Kashuba et al. |
| 5,099,859 A | 3/1992 | Bell |
| 5,100,405 A | 3/1992 | Mclaren |
| 5,100,409 A | 3/1992 | Coates et al. |
| 5,100,417 A | 3/1992 | Cerier et al. |
| 5,100,689 A | 3/1992 | Goldberg et al. |
| 5,101,720 A | 4/1992 | Bianchi |
| 5,102,417 A | 4/1992 | Palmaz |
| 5,102,421 A | 4/1992 | Anspach, Jr. |
| 5,104,383 A | 4/1992 | Shichman |
| 5,108,399 A | 4/1992 | Eitenmuller et al. |
| 5,108,433 A | 4/1992 | May et al. |
| 5,108,441 A | 4/1992 | McDowell |
| 5,111,987 A | 5/1992 | Moeinzadeh et al. |
| 5,116,374 A | 5/1992 | Stone |
| 5,120,175 A | 6/1992 | Arbegast et al. |
| 5,122,122 A | 6/1992 | Allgood |
| 5,122,144 A | 6/1992 | Bert et al. |
| 5,123,520 A | 6/1992 | Schmid et al. |
| 5,123,906 A | 6/1992 | Kelman |
| 5,123,914 A | 6/1992 | Cope |
| 5,123,941 A | 6/1992 | Lauren et al. |
| 5,133,732 A | 7/1992 | Wiktor |
| RE34,021 E | 8/1992 | Mueller |
| 5,135,522 A | 8/1992 | Fahrenkrug et al. |
| 5,139,520 A | 8/1992 | Rosenberg |
| 5,141,520 A | 8/1992 | Goble et al. |
| 5,143,062 A | 9/1992 | Peckham |
| 5,143,093 A | 9/1992 | Sahota |
| 5,147,362 A | 9/1992 | Goble |
| 5,152,744 A | 10/1992 | Krause et al. |
| 5,152,765 A | 10/1992 | Ross et al. |
| 5,152,778 A | 10/1992 | Bales, Jr. et al. |
| 5,154,717 A | 10/1992 | Matsen, III et al. |
| 5,154,720 A | 10/1992 | Trott et al. |
| 5,156,613 A | 10/1992 | Sawyer |
| 5,156,616 A | 10/1992 | Meadows et al. |
| 5,158,553 A | 10/1992 | Berry et al. |
| 5,158,566 A | 10/1992 | Pianetti |
| 5,158,571 A | 10/1992 | Picha |
| 5,158,934 A | 10/1992 | Ammann et al. |
| 5,159,921 A | 11/1992 | Hoover |
| 5,162,506 A | 11/1992 | Hadden |
| 5,163,949 A | 11/1992 | Bonutti |
| 5,163,960 A | 11/1992 | Bonutti |
| 5,170,800 A | 12/1992 | Smith et al. |
| 5,171,243 A | 12/1992 | Kashuba et al. |
| 5,171,244 A | 12/1992 | Caspari et al. |
| 5,171,251 A | 12/1992 | Bregen et al. |
| 5,171,276 A | 12/1992 | Caspari et al. |
| 5,174,300 A | 12/1992 | Bales et al. |
| 1,312,518 A | 1/1993 | Hayhurst |
| 5,176,682 A | 1/1993 | Chow |
| 5,176,684 A | 1/1993 | Ferrante et al. |
| 5,176,702 A | 1/1993 | Bales et al. |
| 5,178,622 A | 1/1993 | Lehner, II |
| 5,179,964 A | 1/1993 | Cook |
| 5,180,388 A | 1/1993 | Di Carlo |
| 5,183,053 A | 2/1993 | Yeh et al. |
| 5,183,464 A | 2/1993 | Dubrul et al. |
| 5,185,001 A | 2/1993 | Galanakis |
| 5,186,178 A | 2/1993 | Yeh et al. |
| 5,192,287 A | 3/1993 | Fournier et al. |
| 5,192,326 A | 3/1993 | Bao et al. |
| 5,192,327 A | 3/1993 | Brantigan |
| 5,195,507 A | 3/1993 | Bilweis |
| 5,195,970 A | 3/1993 | Gahara |
| 5,197,166 A | 3/1993 | Meier et al. |
| 5,197,488 A | 3/1993 | Kovacevic |
| 5,197,955 A | 3/1993 | Stephens et al. |
| 5,197,968 A | 3/1993 | Clement |
| 5,197,971 A | 3/1993 | Bonutti |
| 5,197,987 A | 3/1993 | Koch et al. |
| 5,201,768 A | 4/1993 | Caspari et al. |
| 5,203,784 A | 4/1993 | Ross et al. |
| 5,203,787 A | 4/1993 | Noblitt et al. |
| 5,204,106 A | 4/1993 | Schepers et al. |
| 5,207,692 A | 5/1993 | Kraus et al. |

(56) References Cited

U.S. PATENT DOCUMENTS

| | | |
|---|---|---|
| 5,208,950 A | 5/1993 | Merritt |
| 5,209,776 A | 5/1993 | Bass et al. |
| 5,211,647 A | 5/1993 | Schmieding |
| 5,217,463 A | 6/1993 | Mikhail |
| 5,217,486 A | 6/1993 | Rice et al. |
| 5,217,493 A | 6/1993 | Raad et al. |
| 5,219,359 A | 6/1993 | McQuilkin et al. |
| 5,224,946 A | 7/1993 | Hayhurst et al. |
| 5,226,426 A | 7/1993 | Yoon |
| 5,226,877 A | 7/1993 | Epstein |
| 5,226,899 A | 7/1993 | Lee et al. |
| 5,226,915 A | 7/1993 | Bertin |
| 5,228,459 A | 7/1993 | Caspari et al. |
| 5,234,006 A | 8/1993 | Eaton et al. |
| 5,234,425 A | 8/1993 | Fogarty et al. |
| 5,234,433 A | 8/1993 | Bert et al. |
| 5,236,432 A | 8/1993 | Matsen, III et al. |
| 5,236,438 A | 8/1993 | Wilk |
| 5,236,445 A | 8/1993 | Hayhurst et al. |
| 5,242,902 A | 9/1993 | Murphy et al. |
| 5,244,946 A | 9/1993 | Guest et al. |
| 5,246,441 A | 9/1993 | Ross et al. |
| 5,250,026 A | 10/1993 | Ehrlich et al. |
| 5,250,055 A | 10/1993 | Moore et al. |
| 5,250,070 A | 10/1993 | Parodi |
| 5,254,091 A | 10/1993 | Aliahmad et al. |
| 5,254,113 A | 10/1993 | Wilk |
| 5,258,004 A | 11/1993 | Bales et al. |
| 5,258,007 A | 11/1993 | Spetzler et al. |
| 5,258,015 A | 11/1993 | Li et al. |
| 5,258,016 A | 11/1993 | DiPoto et al. |
| 5,258,031 A | 11/1993 | Salib et al. |
| 5,258,032 A | 11/1993 | Bertin |
| 5,261,914 A | 11/1993 | Warren |
| 5,263,498 A | 11/1993 | Caspari et al. |
| 5,263,987 A | 11/1993 | Shah |
| 5,266,325 A | 11/1993 | Kuzma et al. |
| 5,268,001 A | 12/1993 | Nicholson et al. |
| 5,269,783 A | 12/1993 | Sander |
| 5,269,785 A | 12/1993 | Bonutti |
| 5,269,809 A | 12/1993 | Hayhurst et al. |
| 5,273,524 A | 12/1993 | Fox et al. |
| 5,275,166 A | 1/1994 | Vaitekunas et al. |
| 5,281,235 A | 1/1994 | Haber et al. |
| 5,282,803 A | 2/1994 | Lackey |
| 5,282,832 A | 2/1994 | Toso et al. |
| 5,282,861 A | 2/1994 | Kaplan |
| 5,284,655 A | 2/1994 | Bogdansky et al. |
| 5,285,655 A | 2/1994 | Sung-II et al. |
| 5,290,249 A | 3/1994 | Foster et al. |
| 5,290,281 A | 3/1994 | Tschakaloff |
| 5,295,994 A | 3/1994 | Bonutti |
| 5,298,254 A | 3/1994 | Prewett et al. |
| 2,696,338 A | 4/1994 | Perrin |
| 5,304,119 A | 4/1994 | Balaban et al. |
| 5,304,181 A | 4/1994 | Caspari et al. |
| 5,306,280 A | 4/1994 | Bregen et al. |
| 5,306,301 A | 4/1994 | Graf et al. |
| 5,312,438 A | 5/1994 | Johnson |
| 5,315,741 A | 5/1994 | Dubberke |
| 5,318,588 A | 6/1994 | Horzewski et al. |
| 5,320,611 A | 6/1994 | Bonutti |
| 5,322,505 A | 6/1994 | Krause et al. |
| 5,324,308 A | 6/1994 | Pierce |
| 5,326,361 A | 7/1994 | Hollister |
| 5,328,480 A | 7/1994 | Melker et al. |
| 5,329,846 A | 7/1994 | Bonutti |
| 5,329,924 A | 7/1994 | Bonutti |
| 5,330,468 A | 7/1994 | Burkhart |
| 5,330,476 A | 7/1994 | Hiot et al. |
| 5,330,486 A | 7/1994 | Wilk |
| 5,330,497 A | 7/1994 | Freitas et al. |
| 5,331,975 A | 7/1994 | Bonutti |
| 5,334,146 A | 8/1994 | Ozasa |
| 5,336,231 A | 8/1994 | Adair |
| 5,336,240 A | 8/1994 | Metzler et al. |
| 5,339,799 A | 8/1994 | Kami et al. |
| 5,345,927 A | 9/1994 | Bonutti |
| 5,349,956 A | 9/1994 | Bonutti |
| 5,352,229 A | 10/1994 | Goble et al. |
| 5,354,298 A | 10/1994 | Lee et al. |
| 5,354,302 A | 10/1994 | Ko |
| 5,356,413 A | 10/1994 | Martins et al. |
| 5,360,450 A | 11/1994 | Giannini |
| 5,366,480 A | 11/1994 | Corriveau et al. |
| 5,370,646 A | 12/1994 | Reese et al. |
| 5,370,660 A | 12/1994 | Weinstein et al. |
| 5,370,662 A | 12/1994 | Stone et al. |
| 5,372,146 A | 12/1994 | Branch |
| 5,374,235 A | 12/1994 | Ahrens |
| 5,376,101 A | 12/1994 | Green et al. |
| 5,376,126 A | 12/1994 | Lin |
| 5,379,759 A | 1/1995 | Sewell, Jr. |
| 5,382,254 A | 1/1995 | McGarry et al. |
| 5,383,883 A | 1/1995 | Wilk et al. |
| 5,383,905 A | 1/1995 | Golds et al. |
| 5,383,937 A | 1/1995 | Mikhail |
| RE34,866 E | 2/1995 | Kensey et al. |
| 5,390,683 A | 2/1995 | Pisharodi |
| 5,391,171 A | 2/1995 | Schmieding |
| 5,391,173 A | 2/1995 | Wilk |
| RE34,871 E | 3/1995 | McGuire et al. |
| 5,395,308 A | 3/1995 | Fox et al. |
| 5,395,376 A | 3/1995 | Caspari et al. |
| 5,397,311 A | 3/1995 | Walker et al. |
| 5,397,331 A | 3/1995 | Himpens et al. |
| 5,400,805 A | 3/1995 | Warren |
| 5,403,312 A | 4/1995 | Yates et al. |
| 5,403,317 A | 4/1995 | Bonutti |
| 5,403,348 A | 4/1995 | Bonutti |
| 5,405,359 A | 4/1995 | Pierce |
| 5,411,523 A | 5/1995 | Goble |
| 5,413,585 A | 5/1995 | Pagedas |
| 5,415,663 A | 5/1995 | Luckman et al. |
| 5,417,691 A | 5/1995 | Hayhurst |
| 5,417,700 A | 5/1995 | Egan |
| 5,417,701 A | 5/1995 | Holmes |
| 5,417,712 A | 5/1995 | Whittaker et al. |
| 5,423,796 A | 6/1995 | Shikhman et al. |
| 5,423,819 A | 6/1995 | Small et al. |
| 5,423,860 A | 6/1995 | Lizardi et al. |
| 5,425,733 A | 6/1995 | Schmieding |
| 5,431,670 A | 7/1995 | Holmes |
| 5,439,470 A | 8/1995 | Li et al. |
| 5,441,502 A | 8/1995 | Bartlett |
| 5,441,538 A | 8/1995 | Bonutti |
| 5,443,482 A | 8/1995 | Stone et al. |
| 5,443,512 A | 8/1995 | Parr et al. |
| 5,445,615 A | 8/1995 | Yoon |
| 5,447,503 A | 9/1995 | Miller |
| 5,449,372 A | 9/1995 | Schmaltz et al. |
| 5,449,382 A | 9/1995 | Dayton |
| 5,451,235 A | 9/1995 | Lock |
| 5,453,090 A | 9/1995 | Martinez et al. |
| 5,454,365 A | 10/1995 | Bonutti |
| 5,456,722 A | 10/1995 | Mcleod et al. |
| 5,458,653 A | 10/1995 | Davison |
| 5,462,549 A | 10/1995 | Glock |
| 5,462,561 A | 10/1995 | Voda |
| 5,464,424 A | 11/1995 | O'Donnell, Jr. |
| 5,464,425 A | 11/1995 | Skiba |
| 5,464,426 A | 11/1995 | Bonutti |
| 5,464,427 A | 11/1995 | Curtis et al. |
| 5,470,337 A | 11/1995 | Moss |
| 5,472,444 A | 12/1995 | Huebner et al. |
| 5,474,554 A | 12/1995 | Ku |
| 5,474,559 A | 12/1995 | Bertin et al. |
| 5,478,351 A | 12/1995 | Meade et al. |
| 5,478,353 A | 12/1995 | Yoon |
| 5,480,403 A | 1/1996 | Lee et al. |
| 5,484,437 A | 1/1996 | Michelson |
| 5,486,197 A | 1/1996 | Le et al. |
| 5,487,844 A | 1/1996 | Fujita |
| 5,488,958 A | 2/1996 | Topel et al. |

(56) References Cited

U.S. PATENT DOCUMENTS

| | | |
|---|---|---|
| 5,492,697 A | 2/1996 | Boyan et al. |
| 5,496,292 A | 3/1996 | Burnham |
| 5,496,335 A | 3/1996 | Thomason et al. |
| 5,496,348 A | 3/1996 | Bonutti |
| 5,500,000 A | 3/1996 | Feagin et al. |
| 5,501,700 A | 3/1996 | Hirata |
| 5,504,977 A | 4/1996 | Weppner |
| 5,505,735 A | 4/1996 | Li |
| 5,507,754 A | 4/1996 | Green et al. |
| 5,514,091 A | 5/1996 | Yoon |
| 5,514,153 A | 5/1996 | Bonutti |
| 5,520,700 A | 5/1996 | Beyar et al. |
| 5,522,844 A | 6/1996 | Johnson |
| 5,522,845 A | 6/1996 | Wenstrom, Jr. |
| 5,522,846 A | 6/1996 | Bonutti |
| 5,527,341 A | 6/1996 | Gogolewski et al. |
| 5,527,342 A | 6/1996 | Pietrzak et al. |
| 5,527,343 A | 6/1996 | Bonutti |
| 5,529,075 A | 6/1996 | Clark |
| 5,531,759 A | 7/1996 | Kensey et al. |
| 5,534,012 A | 7/1996 | Bonutti |
| 5,534,028 A | 7/1996 | Bao et al. |
| 5,540,718 A | 7/1996 | Bartlett |
| 5,542,423 A | 8/1996 | Bonutti |
| 5,542,947 A | 8/1996 | Treacy |
| 5,545,178 A | 8/1996 | Kensey et al. |
| 5,545,180 A | 8/1996 | Le et al. |
| 5,545,206 A | 8/1996 | Carson |
| 5,545,222 A | 8/1996 | Bonutti |
| 5,549,630 A | 8/1996 | Bonutti |
| 5,549,631 A | 8/1996 | Bonutti |
| 5,549,689 A | 8/1996 | Epstein et al. |
| 5,550,172 A | 8/1996 | Regula et al. |
| 2,215,943 A | 9/1996 | Collette |
| 5,556,402 A | 9/1996 | Xu |
| 5,562,668 A | 10/1996 | Johnson |
| 5,562,684 A | 10/1996 | Kammerer |
| 5,562,688 A | 10/1996 | Riza |
| 5,569,252 A | 10/1996 | Justin et al. |
| 5,569,259 A | 10/1996 | Ferrante et al. |
| 5,569,305 A | 10/1996 | Bonutti |
| 5,569,306 A | 10/1996 | Thal |
| 5,571,139 A | 11/1996 | Jenkins, Jr. |
| 5,571,196 A | 11/1996 | Stein |
| 5,573,517 A | 11/1996 | Bonutti et al. |
| 5,573,538 A | 11/1996 | Laboureau |
| 5,573,542 A | 11/1996 | Stevens |
| 5,575,801 A | 11/1996 | Habermeyer |
| 5,577,517 A | 11/1996 | Bonutti |
| 5,580,344 A | 12/1996 | Hasson |
| 5,584,835 A | 12/1996 | Greenfield |
| 5,584,860 A | 12/1996 | Goble et al. |
| 5,584,862 A | 12/1996 | Bonutti |
| 5,591,206 A | 1/1997 | Moufarrege |
| 5,593,422 A | 1/1997 | Muijs Van De Moer et al. |
| 5,593,425 A | 1/1997 | Bonutti et al. |
| 5,593,625 A | 1/1997 | Riebel et al. |
| 5,601,557 A | 2/1997 | Hayhurst |
| 5,601,558 A | 2/1997 | Torrie et al. |
| 5,601,565 A | 2/1997 | Huebner et al. |
| 5,601,595 A | 2/1997 | Smith |
| 5,607,427 A | 3/1997 | Tschakaloff |
| 5,609,595 A | 3/1997 | Pennig |
| 5,609,635 A | 3/1997 | Michelson |
| 5,618,314 A | 4/1997 | Harwin et al. |
| 5,620,448 A | 4/1997 | Puddu |
| 5,620,461 A | 4/1997 | Muijs Van De Moer et al. |
| 5,624,462 A | 4/1997 | Bonutti |
| 5,624,463 A | 4/1997 | Stone et al. |
| 5,626,612 A | 5/1997 | Bartlett |
| 5,626,614 A | 5/1997 | Hart |
| 5,626,718 A | 5/1997 | Philippe et al. |
| 5,628,751 A | 5/1997 | Sander et al. |
| 5,630,824 A | 5/1997 | Hart |
| 5,634,926 A | 6/1997 | Jobe |
| 5,643,274 A | 7/1997 | Sander et al. |
| 5,643,293 A | 7/1997 | Kogasaka et al. |
| 5,643,295 A | 7/1997 | Yoon |
| 5,643,320 A | 7/1997 | Lower et al. |
| 5,643,321 A | 7/1997 | McDevitt |
| 5,644,002 A | 7/1997 | Cooper et al. |
| 5,645,553 A | 7/1997 | Kolesa et al. |
| 5,645,588 A | 7/1997 | Graf et al. |
| 5,645,597 A | 7/1997 | Krapiva |
| 5,645,599 A | 7/1997 | Samani |
| 5,649,955 A | 7/1997 | Hashimoto et al. |
| 5,649,963 A | 7/1997 | McDevitt |
| 5,651,377 A | 7/1997 | O'Donnell, Jr. |
| 5,658,313 A | 8/1997 | Thal |
| 5,660,225 A | 8/1997 | Saffran |
| 5,662,658 A | 9/1997 | Wenstrom, Jr. |
| 5,662,710 A | 9/1997 | Bonutti |
| 5,665,089 A | 9/1997 | Dall et al. |
| 5,665,109 A | 9/1997 | Yoon |
| 5,665,112 A | 9/1997 | Thal |
| 5,667,513 A | 9/1997 | Torrie et al. |
| 5,667,520 A | 9/1997 | Bonutti |
| 5,669,909 A | 9/1997 | Zdeblick et al. |
| 5,669,917 A | 9/1997 | Sauer et al. |
| 5,674,240 A | 10/1997 | Bonutti |
| 5,681,310 A | 10/1997 | Yuan et al. |
| 5,681,333 A | 10/1997 | Burkhart et al. |
| 5,681,351 A | 10/1997 | Jamiolkowski et al. |
| 5,681,352 A | 10/1997 | Clancy, III et al. |
| 5,682,886 A | 11/1997 | Delp et al. |
| 5,683,401 A | 11/1997 | Schmieding et al. |
| 5,683,418 A | 11/1997 | Luscombe et al. |
| 5,683,469 A | 11/1997 | Johnson et al. |
| 5,685,820 A | 11/1997 | Riek et al. |
| 5,685,826 A | 11/1997 | Bonutti |
| 5,688,283 A | 11/1997 | Knapp |
| 5,690,654 A | 11/1997 | Ovil |
| 5,690,655 A | 11/1997 | Hart et al. |
| 5,690,674 A | 11/1997 | Diaz |
| 5,690,676 A | 11/1997 | DiPoto et al. |
| 5,693,055 A | 12/1997 | Zahiri et al. |
| 5,694,951 A | 12/1997 | Bonutti |
| 5,697,950 A | 12/1997 | Fucci et al. |
| 5,702,397 A | 12/1997 | Goble et al. |
| 5,702,462 A | 12/1997 | Oberlander |
| 5,707,390 A | 1/1998 | Bonutti |
| 5,707,395 A | 1/1998 | Li |
| 5,713,897 A | 2/1998 | Goble |
| 5,713,903 A | 2/1998 | Sander et al. |
| 5,713,921 A | 2/1998 | Bonutti |
| 5,715,836 A | 2/1998 | Kliegis et al. |
| 5,716,325 A | 2/1998 | Bonutti |
| 5,718,717 A | 2/1998 | Bonutti |
| 5,720,747 A | 2/1998 | Burke |
| 5,720,753 A | 2/1998 | Sander et al. |
| 5,722,978 A | 3/1998 | Jenkins, Jr. |
| 5,723,016 A | 3/1998 | Minns et al. |
| 5,725,529 A | 3/1998 | Nicholson et al. |
| 5,725,541 A | 3/1998 | Anspach, III et al. |
| 5,725,556 A | 3/1998 | Moser et al. |
| 5,725,557 A | 3/1998 | Gatturna et al. |
| 5,725,582 A | 3/1998 | Bevan |
| 5,730,747 A | 3/1998 | Ek et al. |
| 5,733,306 A | 3/1998 | Bonutti |
| 5,735,875 A | 4/1998 | Bonutti et al. |
| 5,735,877 A | 4/1998 | Pagedas |
| 5,735,899 A | 4/1998 | Schwartz et al. |
| 5,741,268 A | 4/1998 | Shutz |
| 5,741,282 A | 4/1998 | Anspach, III et al. |
| 5,752,952 A | 5/1998 | Adamson |
| 5,752,974 A | 5/1998 | Rhee et al. |
| 5,755,809 A | 5/1998 | Cohen et al. |
| 5,762,458 A | 6/1998 | Wang et al. |
| 5,763,416 A | 6/1998 | Bonadio et al. |
| 5,766,221 A | 6/1998 | Benderev et al. |
| 5,766,251 A | 6/1998 | Koshino |
| 5,769,854 A | 6/1998 | Bastian et al. |
| 5,769,894 A | 6/1998 | Ferragamo |
| 5,772,672 A | 6/1998 | Toy et al. |

(56) References Cited

U.S. PATENT DOCUMENTS

| | | |
|---|---|---|
| 5,776,151 A | 7/1998 | Chan |
| 5,779,706 A | 7/1998 | Tschakaloff |
| 5,779,719 A | 7/1998 | Klein et al. |
| 5,779,728 A | 7/1998 | Lunsford et al. |
| 5,782,862 A | 7/1998 | Bonutti |
| 5,782,925 A | 7/1998 | Collazo et al. |
| 5,785,713 A | 7/1998 | Jobe |
| 5,792,096 A | 8/1998 | Rentmeester et al. |
| 5,797,931 A | 8/1998 | Bito et al. |
| 5,797,963 A | 8/1998 | McDevitt |
| 5,800,537 A | 9/1998 | Bell |
| 5,800,544 A | 9/1998 | Demopulos |
| 5,806,518 A | 9/1998 | Mittelstadt |
| 5,807,403 A | 9/1998 | Beyar et al. |
| 5,810,827 A | 9/1998 | Haines et al. |
| 5,810,853 A | 9/1998 | Yoon |
| 5,814,071 A | 9/1998 | McDevitt et al. |
| 5,814,072 A | 9/1998 | Bonutti |
| 5,814,073 A | 9/1998 | Bonutti |
| 5,817,107 A | 10/1998 | Schaller |
| 5,823,994 A | 10/1998 | Sharkey et al. |
| 5,824,009 A | 10/1998 | Fukuda et al. |
| 5,827,318 A | 10/1998 | Bonutti |
| 5,830,125 A | 11/1998 | Scribner et al. |
| 5,836,897 A | 11/1998 | Sakurai et al. |
| 5,839,899 A | 11/1998 | Robinson |
| 5,843,178 A | 12/1998 | Vanney et al. |
| 5,845,645 A | 12/1998 | Bonutti |
| 5,853,422 A | 12/1998 | Huebsch et al. |
| 5,860,997 A | 1/1999 | Bonutti |
| 5,865,834 A | 2/1999 | McGuire |
| 5,866,634 A | 2/1999 | Tokushige et al. |
| 5,868,749 A | 2/1999 | Reed |
| 5,871,018 A | 2/1999 | Delp et al. |
| 5,873,891 A | 2/1999 | Sohn |
| 5,874,235 A | 2/1999 | Chan |
| 5,879,372 A | 3/1999 | Bartlett |
| 5,888,196 A | 3/1999 | Bonutti |
| 5,888,219 A | 3/1999 | Bonutti |
| 5,897,559 A | 4/1999 | Masini |
| 5,897,574 A | 4/1999 | Bonutti |
| 5,899,911 A | 5/1999 | Carter |
| 5,906,579 A | 5/1999 | Vander Salm et al. |
| 5,906,616 A | 5/1999 | Pavlov et al. |
| 5,906,625 A | 5/1999 | Bito et al. |
| 5,911,721 A | 6/1999 | Nicholson et al. |
| 5,919,193 A | 7/1999 | Slavitt |
| 5,919,208 A | 7/1999 | Valenti |
| 5,921,986 A | 7/1999 | Bonutti |
| 5,925,064 A | 7/1999 | Meyers et al. |
| 5,928,267 A | 7/1999 | Bonutti et al. |
| 5,935,094 A | 8/1999 | Zupkas |
| 5,935,131 A | 8/1999 | Bonutti |
| 5,935,149 A | 8/1999 | Ek |
| 5,941,900 A | 8/1999 | Bonutti |
| 5,948,002 A | 9/1999 | Bonutti |
| 5,954,739 A | 9/1999 | Bonutti |
| 5,957,953 A | 9/1999 | DiPoto et al. |
| 5,961,499 A | 10/1999 | Bonutti |
| 5,961,521 A | 10/1999 | Roger |
| 5,961,538 A | 10/1999 | Pedlick et al. |
| 5,968,044 A | 10/1999 | Nicholson et al. |
| 5,968,047 A | 10/1999 | Reed |
| 5,980,520 A | 11/1999 | Vancaillie |
| 5,980,558 A | 11/1999 | Wiley |
| 5,980,559 A | 11/1999 | Bonutti |
| 5,984,967 A | 11/1999 | Zdeblick et al. |
| 5,989,282 A | 11/1999 | Bonutti |
| 5,989,289 A | 11/1999 | Coates et al. |
| 6,007,567 A | 12/1999 | Bonutti |
| 6,007,580 A | 12/1999 | Lehto et al. |
| 6,010,525 A | 1/2000 | Bonutti et al. |
| 6,013,853 A | 1/2000 | Athanasiou et al. |
| 6,017,305 A | 1/2000 | Bonutti |
| 6,017,321 A | 1/2000 | Boone |
| 6,024,746 A | 2/2000 | Katz |
| 6,033,430 A | 3/2000 | Bonutti |
| 6,042,596 A | 3/2000 | Bonutti |
| 6,045,551 A | 4/2000 | Bonutti |
| 6,050,998 A | 4/2000 | Fletcher |
| 6,056,754 A | 5/2000 | Haines et al. |
| 6,056,772 A | 5/2000 | Bonutti |
| 6,056,773 A | 5/2000 | Bonutti |
| 6,059,817 A | 5/2000 | Bonutti et al. |
| 6,063,095 A | 5/2000 | Wang et al. |
| 6,066,175 A | 5/2000 | Henderson et al. |
| 6,068,648 A | 5/2000 | Cole et al. |
| 6,074,409 A | 6/2000 | Goldfarb |
| 6,077,292 A | 6/2000 | Bonutti |
| 6,083,244 A | 7/2000 | Lubbers et al. |
| 6,086,593 A | 7/2000 | Bonutti |
| 6,086,608 A | 7/2000 | Ek et al. |
| 6,090,072 A | 7/2000 | Kratoska et al. |
| 6,099,531 A | 8/2000 | Bonutti |
| 6,099,537 A | 8/2000 | Sugai et al. |
| 6,099,547 A | 8/2000 | Gellman et al. |
| 6,099,550 A | 8/2000 | Yoon |
| 6,102,928 A | 8/2000 | Bonutti |
| 6,102,955 A | 8/2000 | Mendes et al. |
| 6,110,207 A | 8/2000 | Eichhorn et al. |
| 6,117,160 A | 9/2000 | Bonutti |
| 6,120,536 A | 9/2000 | Ding et al. |
| 6,123,710 A | 9/2000 | Pinczewski |
| 6,125,574 A | 10/2000 | Ganaja et al. |
| 6,126,677 A | 10/2000 | Ganaja et al. |
| 6,132,472 A | 10/2000 | Bonutti |
| 6,139,320 A | 10/2000 | Hahn |
| RE36,974 E | 11/2000 | Bonutti |
| 6,152,949 A | 11/2000 | Bonutti |
| 6,159,234 A | 12/2000 | Bonutti et al. |
| 6,171,236 B1 | 1/2001 | Bonutti |
| 6,171,299 B1 | 1/2001 | Bonutti |
| 6,174,313 B1 | 1/2001 | Bonutti |
| 6,187,023 B1 | 2/2001 | Bonutti |
| 6,190,400 B1 | 2/2001 | Van De Moer et al. |
| 6,190,401 B1 | 2/2001 | Green et al. |
| 6,193,754 B1 | 2/2001 | Seedhom |
| 6,203,565 B1 | 3/2001 | Bonutti et al. |
| 6,217,617 B1 | 4/2001 | Bonutti |
| 6,231,592 B1 | 5/2001 | Bonutti et al. |
| 6,235,057 B1 | 5/2001 | Roger et al. |
| 6,238,395 B1 | 5/2001 | Bonutti |
| 6,238,396 B1 | 5/2001 | Lombardo |
| 6,258,091 B1 | 7/2001 | Sevrain et al. |
| 6,277,136 B1 | 8/2001 | Bonutti |
| 6,287,325 B1 | 9/2001 | Bonutti |
| 6,309,405 B1 | 10/2001 | Bonutti |
| 6,312,448 B1 | 11/2001 | Bonutti |
| 6,325,806 B1 | 12/2001 | Fox |
| 6,338,730 B1 | 1/2002 | Bonutti |
| 6,358,266 B1 | 3/2002 | Bonutti |
| 6,361,565 B1 | 3/2002 | Bonutti |
| 6,364,897 B1 | 4/2002 | Bonutti |
| 6,368,343 B1 | 4/2002 | Bonutti et al. |
| 6,398,797 B2 | 6/2002 | Bombard et al. |
| 6,423,063 B1 | 7/2002 | Bonutti |
| 6,428,562 B2 | 8/2002 | Bonutti |
| 6,447,516 B1 | 9/2002 | Bonutti |
| 6,450,985 B1 | 9/2002 | Schoelling et al. |
| 6,451,042 B1 | 9/2002 | Bonutti |
| 6,464,713 B2 | 10/2002 | Bonutti |
| 6,468,289 B1 | 10/2002 | Bonutti |
| 6,468,293 B2 | 10/2002 | Bonutti et al. |
| 6,471,724 B2 | 10/2002 | Zdeblick et al. |
| 6,475,230 B1 | 11/2002 | Bonutti et al. |
| 6,500,195 B2 | 12/2002 | Bonutti |
| 6,503,267 B2 | 1/2003 | Bonutti et al. |
| 6,503,277 B2 | 1/2003 | Bonutti |
| 6,540,786 B2 | 4/2003 | Chibrac et al. |
| 6,543,455 B2 | 4/2003 | Bonutti |
| 6,569,187 B1 | 5/2003 | Bonutti |
| 6,572,635 B1 | 6/2003 | Bonutti |
| 6,575,982 B1 | 6/2003 | Bonutti |
| D477,776 S | 7/2003 | Pontaoe |

(56) References Cited

U.S. PATENT DOCUMENTS

| | | |
|---|---|---|
| 6,585,750 B2 | 7/2003 | Bonutti |
| 6,592,531 B2 | 7/2003 | Bonutti |
| 6,592,609 B1 | 7/2003 | Bonutti |
| 6,607,534 B2 | 8/2003 | Bonutti |
| 6,620,181 B1 | 9/2003 | Bonutti |
| 6,630,000 B1 | 10/2003 | Bonutti |
| 6,635,073 B2 | 10/2003 | Bonutti |
| 6,638,279 B2 | 10/2003 | Bonutti |
| 6,638,309 B2 | 10/2003 | Bonutti |
| 6,652,532 B2 | 11/2003 | Bonutti |
| 6,702,821 B2 | 3/2004 | Bonutti |
| 6,702,856 B2 | 3/2004 | Bonutti |
| 6,719,765 B2 | 4/2004 | Bonutti |
| 6,719,803 B2 | 4/2004 | Bonutti |
| 6,736,853 B2 | 5/2004 | Bonutti |
| 6,770,078 B2 | 8/2004 | Bonutti |
| 6,776,938 B2 | 8/2004 | Bonutti |
| 6,835,198 B2 | 12/2004 | Bonutti |
| 6,860,885 B2 | 3/2005 | Bonutti |
| 6,860,904 B2 | 3/2005 | Bonutti |
| 6,899,722 B2 | 5/2005 | Bonutti |
| 6,905,517 B2 | 6/2005 | Bonutti |
| 6,908,466 B1 | 6/2005 | Bonutti et al. |
| 6,932,835 B2 | 8/2005 | Bonutti et al. |
| 6,942,684 B2 | 9/2005 | Bonutti |
| 6,955,683 B2 | 10/2005 | Bonutti |
| 6,989,029 B2 | 1/2006 | Bonutti |
| 6,990,982 B1 | 1/2006 | Bonutti |
| 6,997,940 B2 | 2/2006 | Bonutti |
| 7,001,385 B2 | 2/2006 | Bonutti |
| 7,004,959 B2 | 2/2006 | Bonutti |
| 7,048,755 B2 | 5/2006 | Bonutti |
| 7,070,557 B2 | 7/2006 | Bonutti |
| 7,087,073 B2 | 8/2006 | Bonutti |
| 7,094,251 B2 | 8/2006 | Bonutti |
| 7,104,996 B2 | 9/2006 | Bonutti |
| 7,114,500 B2 | 10/2006 | Bonutti |
| 7,128,753 B1 | 10/2006 | Bonutti et al. |
| 7,128,763 B1 | 10/2006 | Blatt |
| 7,134,437 B2 | 11/2006 | Bonutti |
| 7,147,652 B2 | 12/2006 | Bonutti et al. |
| 7,208,013 B1 | 4/2007 | Bonutti |
| 7,217,273 B2 | 5/2007 | Bonutti |
| 7,217,290 B2 | 5/2007 | Bonutti |
| 7,311,719 B2 | 12/2007 | Bonutti |
| 7,329,263 B2 | 2/2008 | Bonutti |
| 7,429,266 B2 | 9/2008 | Bonutti |
| 7,462,200 B2 | 12/2008 | Bonutti |
| 7,481,825 B2 | 1/2009 | Bonutti |
| 7,481,831 B2 | 1/2009 | Bonutti |
| 7,510,557 B1 | 3/2009 | Bonutti |
| 7,615,054 B1 | 11/2009 | Bonutti |
| 7,635,390 B1 | 12/2009 | Bonutti |
| 7,708,740 B1 | 5/2010 | Bonutti |
| 7,708,741 B1 | 5/2010 | Bonutti |
| 7,727,283 B2 | 6/2010 | Bonutti |
| 7,749,229 B1 | 7/2010 | Bonutti |
| 7,780,670 B2 | 8/2010 | Bonutti |
| 7,806,896 B1 | 10/2010 | Bonutti |
| 7,806,897 B1 | 10/2010 | Bonutti |
| 7,828,852 B2 | 11/2010 | Bonutti |
| 7,837,736 B2 | 11/2010 | Bonutti |
| 7,854,750 B2 | 12/2010 | Bonutti et al. |
| 7,879,072 B2 | 2/2011 | Bonutti et al. |
| 7,892,236 B1 | 2/2011 | Bonutti |
| 7,892,261 B2 | 2/2011 | Bonutti |
| 7,896,880 B2 | 3/2011 | Bonutti |
| 7,931,690 B1 | 4/2011 | Bonutti |
| 7,959,635 B1 | 6/2011 | Bonutti |
| 7,967,820 B2 | 6/2011 | Bonutti et al. |
| RE43,143 E | 1/2012 | Hayhurst |
| 8,128,669 B2 | 3/2012 | Bonutti |
| 8,133,229 B1 | 3/2012 | Bonutti |
| 8,147,514 B2 | 4/2012 | Bonutti |
| 8,162,977 B2 | 4/2012 | Bonutti et al. |
| 8,425,522 B2 | 4/2013 | Bonutti |
| 8,486,066 B2 | 7/2013 | Bonutti |
| 8,496,657 B2 | 7/2013 | Bonutti et al. |
| 8,617,185 B2 | 12/2013 | Bonutti |
| 8,623,030 B2 | 1/2014 | Bonutti |
| 8,632,552 B2 | 1/2014 | Bonutti |
| 8,641,726 B2 | 2/2014 | Bonutti |
| 8,690,944 B2 | 4/2014 | Bonutti |
| 2001/0023371 A1 | 9/2001 | Bonutti |
| 2002/0029055 A1 | 3/2002 | Bonutti |
| 2002/0040246 A1 | 4/2002 | Bonutti |
| 2002/0095160 A1 | 7/2002 | Bonutti |
| 2003/0009147 A1 | 1/2003 | Bonutti |
| 2003/0023260 A1 | 1/2003 | Bonutti |
| 2003/0032975 A1 | 2/2003 | Bonutti |
| 2003/0181800 A1 | 9/2003 | Bonutti |
| 2004/0010287 A1 | 1/2004 | Bonutti |
| 2004/0097794 A1 | 5/2004 | Bonutti |
| 2004/0098016 A1 | 5/2004 | Bonutti |
| 2004/0127930 A1 | 7/2004 | Bonutti |
| 2004/0138689 A1 | 7/2004 | Bonutti |
| 2004/0138690 A1 | 7/2004 | Bonutti |
| 2004/0143285 A1 | 7/2004 | Bonutti |
| 2004/0167548 A1 | 8/2004 | Bonutti |
| 2004/0172033 A1 | 9/2004 | Bonutti |
| 2004/0193181 A1 | 9/2004 | Bonutti |
| 2004/0220616 A1 | 11/2004 | Bonutti |
| 2004/0230223 A1 | 11/2004 | Bonutti |
| 2004/0254582 A1 | 12/2004 | Bonutti |
| 2005/0216059 A1 | 9/2005 | Bonutti et al. |
| 2005/0222620 A1 | 10/2005 | Bonutti |
| 2005/0240227 A1 | 10/2005 | Bonutti |
| 2005/0267534 A1 | 12/2005 | Bonutti |
| 2006/0015108 A1 | 1/2006 | Bonutti |
| 2006/0089646 A1 | 4/2006 | Bonutti |
| 2006/0142799 A1 | 6/2006 | Bonutti |
| 2006/0167495 A1 | 7/2006 | Bonutti |
| 2006/0200199 A1 | 9/2006 | Bonutti et al. |
| 2006/0212073 A1 | 9/2006 | Bonutti |
| 2006/0229623 A1 | 10/2006 | Bonutti et al. |
| 2006/0235470 A1 | 10/2006 | Bonutti |
| 2006/0241695 A1 | 10/2006 | Bonutti |
| 2006/0265009 A1 | 11/2006 | Bonutti |
| 2006/0265011 A1 | 11/2006 | Bonutti |
| 2007/0088362 A1 | 4/2007 | Bonutti et al. |
| 2007/0102005 A1 | 5/2007 | Bonutti |
| 2007/0208378 A1 | 9/2007 | Bonutti et al. |
| 2008/0021474 A1 | 1/2008 | Bonutti |
| 2008/0039845 A1 | 2/2008 | Bonutti |
| 2008/0039873 A1 | 2/2008 | Bonutti et al. |
| 2008/0047567 A1 | 2/2008 | Bonutti |
| 2008/0051799 A1 | 2/2008 | Bonutti |
| 2008/0058822 A1 | 3/2008 | Bonutti |
| 2008/0065140 A1 | 3/2008 | Bonutti |
| 2008/0103519 A1 | 5/2008 | Bonutti |
| 2008/0108916 A1 | 5/2008 | Bonutti |
| 2008/0114399 A1 | 5/2008 | Bonutti |
| 2008/0140116 A1 | 6/2008 | Bonutti |
| 2008/0140117 A1 | 6/2008 | Bonutti |
| 2010/0211120 A1 | 8/2010 | Bonutti et al. |
| 2010/0312350 A1 | 12/2010 | Bonutti |
| 2011/0060375 A1 | 3/2011 | Bonutti |
| 2011/0295253 A1 | 12/2011 | Bonutti et al. |
| 2012/0010623 A1 | 1/2012 | Bonutti |
| 2012/0165841 A1 | 6/2012 | Bonutti |
| 2012/0191140 A1 | 7/2012 | Bonutti |
| 2012/0215226 A1 | 8/2012 | Bonutti |
| 2012/0215233 A1 | 8/2012 | Bonutti et al. |
| 2012/0221017 A1 | 8/2012 | Bonutti |
| 2013/0144389 A1 | 6/2013 | Bonutti |
| 2013/0226185 A1 | 8/2013 | Bonutti |
| 2013/0226311 A1 | 8/2013 | Bonutti |
| 2014/0018852 A1 | 1/2014 | Bonutti |
| 2014/0018854 A1 | 1/2014 | Bonutti |

(56) References Cited

U.S. PATENT DOCUMENTS

| | | |
|---|---|---|
| 2014/0025110 A1 | 1/2014 | Bonutti |
| 2014/0025111 A1 | 1/2014 | Bonutti |
| 2014/0025112 A1 | 1/2014 | Bonutti |

FOREIGN PATENT DOCUMENTS

| | | |
|---|---|---|
| CA | 2680827 | 9/2008 |
| CA | 2698057 | 3/2009 |
| CH | 117960 A | 5/1927 |
| DE | 337437 C | 5/1921 |
| DE | 605255 C | 11/1934 |
| DE | 1903016 U | 10/1964 |
| DE | 1903316 | 10/1964 |
| DE | 1903016 A1 | 8/1970 |
| DE | 2411226 A1 | 9/1974 |
| DE | 32 11 682 | 10/1983 |
| DE | 35 17 204 A1 | 11/1986 |
| DE | 37 07 787 A1 | 9/1988 |
| DE | 37 22 538 A1 | 1/1989 |
| DE | 90 02 844.9 U1 | 1/1991 |
| EP | 0 010 650 A1 | 5/1980 |
| EP | 0 192 576 A1 | 8/1986 |
| EP | 0 283 661 A2 | 9/1988 |
| EP | 0 287 998 A2 | 10/1988 |
| EP | 0 418 147 A1 | 3/1991 |
| EP | 0 699 416 | 3/1996 |
| EP | 784454 | 5/1996 |
| EP | 0 773 004 A1 | 5/1997 |
| EP | 1614525 | 1/2006 |
| EP | 1988837 | 8/2007 |
| EP | 2134294 | 12/2009 |
| FR | 325846 A | 5/1903 |
| FR | 726041 A | 5/1932 |
| FR | 1 111 677 A | 3/1956 |
| FR | 2 344 267 A1 | 10/1977 |
| FR | 2 580 504 A1 | 10/1986 |
| FR | 2 682 287 A1 | 4/1993 |
| FR | 2 717 368 A1 | 3/1994 |
| FR | 2 696 338 | 4/1994 |
| FR | 2 728 779 A1 | 1/1995 |
| FR | 2 736 257 A1 | 7/1995 |
| FR | 2 750 031 A1 | 6/1996 |
| FR | 2 771 621 A1 | 11/1997 |
| FR | 2 785 171 A1 | 10/1998 |
| GB | 214913 A | 5/1924 |
| GB | 2 093 701 A | 9/1982 |
| GB | 2 306 110 A | 4/1997 |
| JP | S6429266 A | 1/1989 |
| JP | 8-140982 | 6/1996 |
| JP | H08173436 | 7/1996 |
| JP | 3738221 | 1/2006 |
| SU | 184396 | 7/1966 |
| SU | 1323090 A1 | 7/1987 |
| SU | 1367947 A1 | 1/1988 |
| WO | WO 87/01270 A1 | 3/1987 |
| WO | WO 88/01517 A1 | 3/1988 |
| WO | WO 91/12779 | 9/1991 |
| WO | WO 93/23094 | 11/1993 |
| WO | WO 94/08642 A1 | 4/1994 |
| WO | WO 95/16398 | 6/1995 |
| WO | WO 95/31941 | 11/1995 |
| WO | WO 96/14802 A1 | 5/1996 |
| WO | WO 96/29029 | 9/1996 |
| WO | WO 97/12779 | 4/1997 |
| WO | WO 97/20522 | 6/1997 |
| WO | WO 97/39700 | 10/1997 |
| WO | WO 97/49347 | 12/1997 |
| WO | WO 98/11838 A1 | 3/1998 |
| WO | WO 98/26720 | 6/1998 |
| WO | WO 01/34036 A1 | 5/2001 |
| WO | WO 02/053011 A2 | 7/2002 |
| WO | WO 2007/092869 A2 | 8/2007 |
| WO | WO 2007/092869 A3 | 8/2007 |
| WO | WO 2008/116203 | 9/2008 |
| WO | WO 2009/029908 | 3/2009 |
| WO | WO 2010/099222 | 2/2010 |

OTHER PUBLICATIONS

Copending U.S. Appl. No. 09/556,458, Non-Final Rejection mailed Sep. 25, 2002.
Copending U.S. Appl. No. 09/556,458, Response to Office Action Dec. 26, 2002.
Copending U.S. Appl. No. 10/614,352, Examiner Interview Summary Jul. 31, 2007.
Copending U.S. Appl. No. 10/614,352, Final Office Action Jul. 12, 2010.
Copending U.S. Appl. No. 10/614,352, Final Rejection mailed Jan. 25, 2007.
Copending U.S. Appl. No. 10/614,352, Final Rejection mailed Apr. 14, 2009.
Copending U.S. Appl. No. 10/614,352, Final Rejection mailed Oct. 2, 2007.
Copending U.S. Appl. No. 10/614,352, non Final Office Action Aug. 10, 2011.
Copending U.S. Appl. No. 10/614,352, Non-Final Rejection mailed Jan. 15, 2008.
Copending U.S. Appl. No. 10/614,352, Non-Final Rejection mailed Apr. 17, 2007.
Copending U.S. Appl. No. 10/614,352, Non-Final Rejection mailed Aug. 1, 2006.
Copending U.S. Appl. No. 10/614,352, Non-Final Rejection mailed Aug. 21, 2008.
Copending U.S. Appl. No. 10/614,352, Non-Final Rejection mailed Nov. 24, 2009.
Copending U.S. Appl. No. 10/614,352, Non-Final Rejection mailed Dec. 1, 2005.
Copending U.S. Appl. No. 10/614,352, Request for Continued Examination Sep. 14, 2009.
Copending U.S. Appl. No. 10/614,352, Request for Continued Examination Oct. 30, 2007.
Copending U.S. Appl. No. 10/614,352, Response to Office Action Mar. 1, 2006.
Copending U.S. Appl. No. 10/614,352, Response to Office Action Mar. 26, 2007.
Copending U.S. Appl. No. 10/614,352, Response to Office Action Apr. 26, 2010.
Copending U.S. Appl. No. 10/614,352, Response to Office Action May 15, 2008.
Copending U.S. Appl. No. 10/614,352, Response to Office Action Jul. 17, 2007.
Copending U.S. Appl. No. 10/614,352, Response to Office Action Sep. 14, 2009.
Copending U.S. Appl. No. 10/614,352, Response to Office Action Oct. 30, 2007.
Copending U.S. Appl. No. 10/614,352, Response to Office Action Nov. 1, 2006.
Copending U.S. Appl. No. 10/614,352, Response to Office Action Dec. 22, 2008.
Copending U.S. Appl. No. 11/931,823, final Office Action mailed Aug. 2, 2011.
Copending U.S. Appl. No. 11/931,823, Office Action mailed Nov. 24, 2010.
Copending U.S. Appl. No. 11/931,823, Response to Office Action Aug. 9, 2010.
Copending U.S. Appl. No. 11/931,823, RestrictionElect dated Jun. 8, 2010.
Copending U.S. Appl. No. 11/187,482 Response to Office Action Jun. 21, 2011.
Copending U.S. Appl. No. 10/413,696, Non-Final Rejection mailed Sep. 23, 2005.
Copending U.S. Appl. No. 10/413,696, Requirement for Restriction Jun. 8, 2005.
Copending U.S. Appl. No. 10/413,696, Response to Office Action Jul. 5, 2005.

(56) References Cited

OTHER PUBLICATIONS

Copending U.S. Appl. No. 10/413,696, Response to Office Action Dec. 20, 2005.
Copending U.S. Appl. No. 11/460,650, mailed Dec. 23, 2009.
Copending U.S. Appl. No. 11/460,650, Final Rejection mailed Apr. 20, 2010.
Copending U.S. Appl. No. 11/460,650, Final Rejection mailed Aug. 29, 2008.
Copending U.S. Appl. 11/460,650, Non-Final Rejection mailed Mar. 10, 2009.
Copending U.S. Appl. No. 11/460,650, Non-Final Rejection mailed May 30, 2007.
Copending U.S. Appl. No. 11/460,650, Non-Final Rejection mailed Sep. 16, 2009.
Copending U.S. Appl. No. 11/460,650, Non-Final Rejection mailed Dec. 28, 2007.
Copending U.S. Appl. No. 11/460,650, Request for Continued Examination Jan. 29, 2009.
Copending U.S. Appl. No. 11/460,650, Response to Office Action Jan. 12, 2010.
Copending U.S. Appl. No. 11/460,650, Response to Office Action Jan. 29, 2009.
Copending U.S. Appl. No. 11/460,650, Response to Office Action Mar. 28, 2008.
Copending U.S. Appl. No. 11/460,650, Response to Office Action Jun. 10, 2009.
Copending U.S. Appl. No. 11/460,650, Response to Office Action Oct. 1, 2007.
Copending U.S. Appl. No. 11/461,110, Final Rejection mailed Dec. 8, 2009.
Copending U.S. Appl. No. 11/461,110, Non-Final Rejection mailed Apr. 22, 2009.
Copending U.S. Appl. No. 11/461,110, Non-Final Rejection mailed Jun. 6, 2008.
Copending U.S. Appl. No. 11/461,110, Request for Continued Examination Mar. 12, 2008.
Copending U.S. Appl. No. 11/461,110, Request for Continued Examination Jun. 8, 2010.
Copending U.S. Appl. No. 11/461,110, Response to Office Action Mar. 12, 2008.
Copending U.S. Appl. No. 11/461,110, Response to Office Action Jun. 8, 2010.
Copending U.S. Appl. No. 11/461,110, Response to Office Action Sep. 22, 2009.
Copending U.S. Appl. No. 11/461,110, Response to Office Action Oct. 6, 2008.
Copending U.S. Appl. No. 11/461,110, Response to Office Action Oct. 15, 2007.
Copending U.S. Appl. No. 11/461,110, Final Rejection mailed Dec. 12, 2007.
Copending U.S. Appl. No. 11/461,110, Non-Final Rejection mailed May 14, 2007.
Copending U.S. Appl. No. 11/930,621, Final Rejection Jun. 22, 2010.
Copending U.S. Appl. No. 11/930,621, Non-Final Rejection mailed Sep. 21, 2009.
Copending U.S. Appl. No. 11/930,621, Response to Office Action Mar. 22, 2010.
Copending U.S. Appl. No. 09/524,397, Final Rejection mailed Jun. 15, 2001.
Copending U.S. Appl. No. 09/524,397, Non-Final Rejection mailed Dec. 18, 2000.
Copending U.S. Appl. No. 09/524,397, Response to Office Action Mar. 19, 2001.
Copending U.S. Appl. No. 09/524,397, Response to Office Action Oct. 15, 2001.
Copending U.S. Appl. No. 10/458,117, Advisory Action Jan. 20, 2006.
Copending U.S. Appl. No. 10/458,117, Examiner Interview Summary mailed May 16, 2008.
Copending U.S. Appl. No. 10/458,117, Non-Final Rejection mailed Mar. 22, 2005.
Copending U.S. Appl. No. 10/458,117, Non-Final Rejection mailed Nov. 15, 2006.
Copending U.S. Appl. No. 10/458,117, Request for Continued Examination Feb. 26, 2008.
Copending U.S. Appl. No. 10/458,117, Request for Continued Examination Feb. 21, 2006.
Copending U.S. Appl. No. 10/458,117, Request for Continued Examination Aug. 3, 2007.
Copending U.S. Appl. No. 10/458,117, Response to Office Action Feb. 13, 2007.
Copending U.S. Appl. No. 10/458,117, Response to Office Action Jun. 22, 2005.
Copending U.S. Appl. No. 10/458,117, Response to Office Action Aug. 3, 2007.
Copending U.S. Appl. No. 10/458,117, Response to Office Action Nov. 8, 2005.
Copending U.S. Appl. No. 10/458,117, Final Rejection mailed May 3, 2007.
Copending U.S. Appl. No. 10/458,117, Final Rejection mailed Sep. 8, 2005.
Copending U.S. Appl. No. 11/370,775, mailed Oct. 29, 2007.
Copending U.S. Appl. No. 11/370,775, mailed Apr. 24, 2008.
Copending U.S. Appl. No. 11/370,775, mailed Feb. 27, 2009.
Copending U.S. Appl. No. 11/370,775, Examiner Interview Summary mailed Aug. 28, 2009.
Copending U.S. Appl. No. 11/370,775, Non-Final Rejection mailed Feb. 6, 2007.
Copending U.S. Appl. No. 11/370,775, Non-Final Rejection mailed Jan. 22, 2008.
Copending U.S. Appl. No. 11/370,775, Non-Final Rejection mailed Oct. 15, 2008.
Copending U.S. Appl. No. 11/370,775, Non-Final Rejection mailed Nov. 6, 2009.
Copending U.S. Appl. No. 11/370,775, Response to Office Action Jun. 4, 2007.
Copending U.S. Appl. No. 11/370,775, Response to Office Action Oct. 26, 2007.
Copending U.S. Appl. No. 11/370,775, Response to Office Action May 22, 2008.
Copending U.S. Appl. No. 11/370,775, Response to Office Action Jan. 15, 2009.
Copending U.S. Appl. No. 11/370,775, Response to Office Action Aug. 13, 2009.
Copending U.S. Appl. No. 11/370,775, Response to Office Action May 6, 2010.
Copending U.S. Appl. No. 11/370,775, Supplemental Response to Office Action Jan. 30, 2009.
Copending U.S. Appl. No. 11/370,775, Final Rejection mailed Aug. 31, 2007.
Copending U.S. Appl. No. 11/370,775, Final Rejection mailed Mar. 13, 2009.
Copending U.S. Appl. No. 11/370,775, Request for Continued Examination Oct. 26, 2007.
Copending U.S. Appl. No. 11/370,775, Request for Continued Examination Jan. 10, 2011.
Copending U.S. Appl. No. 11/370,775, Request for Continued Examination Aug. 13, 2009.
Copending U.S. Appl. No. 11/456,132, mailed Aug. 28, 2009.
Copending U.S. Appl. No. 11/456,132, Request for Continued Examination Jun. 11, 2008.
Copending U.S. Appl. No. 11/456,132, Response to Office Action Jan. 7, 2009.
Copending U.S. Appl. No. 11/456,132, Response filed Jan. 18, 2012.
Copending U.S. Appl. No. 11/456,132, Response to Office Action Apr. 14, 2011.
Copending U.S. Appl. No. 11/456,132, Response to Office Action Apr. 19, 2010.
Copending U.S. Appl. No. 11/456,132, Response to Office Action Jun. 11, 2008.
Copending U.S. Appl. No. 11/456,132, Response to Office Action Aug. 13, 2009.

(56) References Cited

OTHER PUBLICATIONS

Copending U.S. Appl. No. 11/456,132, Response to Office Action Nov. 19, 2007.
Copending U.S. Appl. No. 11/456,132, Final Rejection mailed Mar. 11, 2008.
Copending U.S. Appl. No. 11/456,132, Final Rejection mailed Dec. 18, 2009.
Copending U.S. Appl. No. 11/456,132, Non-Final Rejection mailed Mar. 13, 2009.
Copending U.S. Appl. No. 11/456,132, Non-Final Rejection mailed Jun. 18, 2007.
Copending U.S. Appl. No. 11/456,132, Non-Final Rejection mailed Oct. 7, 2008.
Copending U.S. Appl. No. 11/456,221, Final Rejection mailed Feb. 22, 2008.
Copending U.S. Appl. No. 11/456,221, Final Rejection mailed Mar. 24, 2010.
Copending U.S. Appl. No. 11/456,221, Non-Final Rejection mailed Jul. 6, 2009.
Copending U.S. Appl. No. 11/456,221, Non-Final Rejection mailed Jul. 9, 2007.
Copending U.S. Appl. No. 11/456,221, Non-Final Rejection mailed Oct. 29, 2008.
Copending U.S. Appl. No. 11/456,221, Request for Continued Examination Jun. 19, 2008.
Copending U.S. Appl. No. 11/456,221, Response to Office Action Jan. 6, 2010.
Copending U.S. Appl. No. 11/456,221, Response to Office Action Mar. 30, 2009.
Copending U.S. Appl. No. 11/456,221, Response to Office Action May 22, 2008.
Copending U.S. Appl. No. 11/456,221, Response to Office Action Nov. 9, 2007.
Copending U.S. Appl. No. 11/932,051, Final Office Action mailed Jun. 9, 2011.
Copending U.S. Appl. No. 11/932,051, RCE Response Dec. 9, 2011.
Copending U.S. Appl. No. 11/932,051, Requirement for Restriction Jan. 22, 2010.
Copending U.S. Appl. No. 10/228,855, Non-Final Rejection mailed Sep. 28, 2005.
Copending U.S. Appl. No. 10/228,855, Response to Office Action Dec. 28, 2005.
Copending U.S. Appl. No. 11/465,199, Response to Office Action Jun. 28, 2010.
Copending U.S. Appl. No. 11/465,199, Non-Final Rejection mailed Dec. 28, 2009.
Copending U.S. Appl. No. 11/932,602, Final Response to Office Action Jun. 10, 2011.
Copending U.S. Appl. No. 11/932,602, non final Office Action Oct. 6, 2010.
Copending U.S. Appl. No. 11/932,602, Response to Office Action Apr. 6, 2011.
Copending U.S. Appl. No. 12/359,364, Final Office Action Apr. 7, 2011.
Copending U.S. Appl. No. 11/438,537, RCE Response Nov. 21, 2011.
Copending U.S. Appl. No. 11/932,907, RCE Response Sep. 15, 2011.
Copending U.S. Appl. No. 11/932,907, non-final Office Action Nov. 17, 2010.
Copending U.S. Appl. No. 11/932,907, Response to Office Action Apr. 18, 2011.
Copending U.S. Appl. No. 11/133,730, Final Office action Aug. 17, 2011.
Copending U.S. Appl. No. 11/169,475, Response Sep. 2, 2011.
Copending U.S. Appl. No. 11/169,475, Office Action Mar. 2, 2011.
Copending U.S. Appl. No. 11/126,543, non Final Office Action Aug. 10, 2011.
Copending U.S. Appl. No. 11/126,543, RCE Response filed Jun. 30, 2011.
Copending U.S. Appl. No. 10/780,444, Examiner Interview Summary mailed Nov. 20, 2009.
Copending U.S. Appl. No. 10/780,444, Final Rejection mailed Mar. 30, 2010.
Copending U.S. Appl. No. 10/780,444, Final Rejection mailed Dec. 23, 2008.
Copending U.S. Appl. No. 10/780,444, nonFinal Office Action Aug. 9, 2011.
Copending U.S. Appl. No. 10/780,444, Non-Final Rejection mailed Mar. 11, 2008.
Copending U.S. Appl. 10/780,444, Non-Final Rejection mailed Jul. 7, 2009.
Copending U.S. Appl. No. 10/780,444, Request for Continued Examination Apr. 23, 2009.
Copending U.S. Appl. No. 10/780,444, Requirement for Restriction Sep. 12, 2007.
Copending U.S. Appl. No. 10/780,444, Requirement for Restriction Apr. 10, 2007.
Copending U.S. Appl. No. 10/780,444, Response filed Feb. 9, 2012.
Copending U.S. Appl. No. 10/780,444, Response to Office Action Apr. 23, 2009.
Copending U.S. Appl. No. 10/780,444, Response to Office Action May 10, 2007.
Copending U.S. Appl. No. 10/780,444, Response to Office Action Jul. 9, 2008.
Copending U.S. Appl. No. 10/780,444, Response to Office Action Oct. 12, 2007.
Copending U.S. Appl. No. 10/780,444, Response to Office Action Dec. 4, 2009.
Copending U.S. Appl. No. 10/779,978, Non-Final Office Action mailed Jan. 13, 2011.
Copending U.S. Appl. No. 10/779,978, Final Rejection mailed Feb. 3, 2009.
Copending U.S. Appl. No. 10/779,978, Final Rejection mailed May 14, 2010.
Copending U.S. Appl. No. 10/779,978, Non-Final Rejection mailed Jun. 18, 2008.
Copending U.S. Appl. No. 10/779,978, Non-Final Rejection mailed Aug. 3, 2007.
Copending U.S. Appl. No. 10/779,978, Non-Final Rejection mailed Oct. 1, 2009.
Copending U.S. Appl. No. 10/779,978, Request for Continued Examination Jul. 6, 2009.
Copending U.S. Appl. No. 10/779,978, Requirement for Restriction Apr. 20, 2007.
Copending U.S. Appl. No. 10/779,978, Response to Office Action Feb. 1, 2010.
Copending U.S. Appl. No. 10/779,978, Response to Office Action Mar. 25, 2008.
Copending U.S. Appl. No. 10/779,978, Response to Office Action May 21, 2007.
Copending U.S. Appl. No. 10/779,978, Response to Office Action Jul. 6, 2009.
Copending U.S. Appl. No. 10/779,978, Response to Office Action Jul. 13, 2011.
Copending U.S. Appl. No. 10/779,978, Response to Office Action Oct. 20, 2008.
Copending U.S. Appl. No. 10/779,978, Response to Office Action Dec. 3, 2007.
Copending U.S. Appl. No. 10/797,685, Examiner Interview Summary mailed Sep. 11, 2007.
Copending U.S. Appl. No. 10/797,685, Final Rejection mailed Apr. 25, 2007.
Copending U.S. Appl. No. 10/797,685, Non-Final Rejection mailed Nov. 17, 2006.
Copending U.S. Appl. No. 10/797,685, Response to Office Action Feb. 20, 2007.
Copending U.S. Appl. No. 10/797,685, Response to Office Action Aug. 27, 2007.
Copending U.S. Appl. No. 11/874,323, Office Action mailed Jul. 6, 2011.
Copending U.S. Appl. 11/874,323, Response filed Apr. 21, 2011.

(56) References Cited

OTHER PUBLICATIONS

Copending U.S. Appl. No. 11/258,795, Non-Final Office Action mailed Apr. 26, 2011.
Copending U.S. Appl. No. 11/202,294, Office Action mailed Jun. 24, 2011.
Copending U.S. Appl. No. 11/202,294, Response filed Dec. 24, 2011.
Copending U.S. Appl. No. 11/358,399, non Final Office Action Jan. 3, 2011.
Copending U.S. Appl. No. 11/358,399, Response filed Jul. 5, 2011.
Copending U.S. Appl. No. 11/671,556, Final Office Action mailed Nov. 12, 2010.
Copending U.S. Appl. No. 11/671,556, Response filed Aug. 23, 2010.
Copending U.S. Appl. No. 11/671,556, Non-Final Rejection mailed Feb. 22, 2010.
Copending U.S. Appl. No. 11/671,556, Requirement for Restriction Sep. 1, 2009.
Copending U.S. Appl. No. 11/671,556, Response to Office Action Nov. 2, 2009.
Copending U.S. Appl. No. 11/416,618, Examiner Interview Summary mailed Apr. 15, 2010.
Copending U.S. Appl. No. 11/416,618, Final Rejection mailed Jun. 24, 2009.
Copending U.S. Appl. No. 11/416,618, Non-Final Rejection mailed Oct. 13, 2009.
Copending U.S. Appl. No. 11/416,618, Non-Final Rejection mailed Nov. 26, 2008.
Copending U.S. Appl. No. 11/416,618, Response to Office Action Mar. 15, 2010.
Copending U.S. Appl. No. 11/416,618, Response to Office Action Mar. 26, 2009.
Copending U.S. Appl. No. 11/416,618, Response to Office Action Apr. 16, 2010.
Copending U.S. Appl. No. 11/416,618, Response to Office Action Sep. 24, 2009.
Copending U.S. Appl. No. 11/416,618, Request for Continued Examination Dec. 8, 2011.
Copending U.S. Appl. No. 11/689,670, Final Office Action mailed Mar. 17, 2011.
Copending U.S. Appl. No. 11/689,670, RCE Response Sep. 19, 2011.
Copending U.S. Appl. No. 11/689,670, Requirement for Restriction Mar. 15, 2010.
Copending U.S. Appl. No. 11/689,670, Response to Office Action Jan. 3, 2011.
Copending U.S. Appl. No. 11/689,670, Response to Office Action Apr. 15, 2010.
Copending U.S. Appl. No. 12/202,210, Requirement for Restriction mailed Aug. 16, 2011.
Copending U.S. Appl. No. 12/202,210, Response filed Dec. 16, 2011.
Co-pending U.S. Appl. No. 11/438,537, Supplemental Final Rejection mailed Sep. 25, 2009.
File History of U.S. Patent No. 5,403,348; U.S. Appl. No. 08/062,295, filed May 14, 1993; 231 pages.
File History of U.S. Patent No. 5,522,846; U.S. Appl. No. 08/402,352, filed Mar. 10, 1995; 215 pages.
History of U.S. Patent No. 5,527,343; U.S. Appl. No. 08/344,466, filed Nov. 23, 1994; 246 pages.
File History of U.S. Patent No. 5,549,630; U.S. Appl. No. 08/291,970, filed Aug. 17, 1994; 276 pages.
File History of U.S. Patent No. 5,980,559; U.S. Appl. No. 08/964,167, filed Nov. 4, 1997; 57 pages.
File History of U.S. Patent No. 6,500,195; U.S. Appl. No. 09/872,033, filed Jun. 1, 2001; 522 pages.
File History of U.S. Patent No. 7,087,073; U.S. Appl. No. 10/413,696, filed Apr. 14, 2003; 13 pages.
Petition for Inter Partes Review of U.S. Patent No. 5,980,559 Under 35 U.S.C. § 312 and 37 C.F.R. § 42.104; filed Sep. 24, 2013; IPR2013-00603; with exhibits, 382 pages.
Declaration of David Kaplan, PH.D. Regarding U.S. Patent No. 5,980,559, IPR 2013-00603, Sep. 24, 2013; 86 pages.
Petition for Inter Partes Review of U.S. Patent No. 7,087,073 Under 35 U.S.C. § 312 and 37 C.F.R. § 42.104; filed Sep. 24, 2013; IPR2013-00604; with exhibits, 243 pages.
Declaration of Wayne J. Sebastianelli, MD Regarding U.S. Patent No. 7,087,073, Sep. 24, 2013, IPR 2013-00604; 82 pages.
Petition for Inter Partes Review of U.S. Patent No. 6,500,195 Under 35 U.S.C. § 312 and 37 C.F.R. § 42.104; filed Sep. 25, 2013; IPR2013-00624; with exhibits, 1152 pages.
Declaration of Dr. Philip Hardy in Support of Petition for Inter Partes Review of U.S. Patent No. 6,500,195, IPR 2013-00624; Sep. 25, 2013; 28 pages.
Petition for Inter Partes Review of U.S. Patent No. 5,527,343 Under 35 U.S.C. § 312 and 37 C.F.R. § 42.104; filed Sep. 26, 2013; IPR2013-00628; with exhibits, 882 pages.
Declaration of Dr. Philip Hardy in Support of Petition for Inter Partes Review of U.S. Patent No. 5,527,343, IPR 2013-00628, Sep. 25, 2013; 65 pages.
Corrected Petition for Inter Partes Review of U.S. Patent No. 5,921,986 Under 35 U.S.C. §§ 311-319 and 37 C.F.R. § 42.100 Et Seq.; filed Oct. 11, 2013; IPR2013-00631; with exhibits, 285 pages.
Expert Declaration of Steve E. Jordan, MD, for Inter Partes Review of U.S. Patent No. 5,921,986, IPR 2013-00631, Sep. 24, 2013; 39 pages.
Corrected Petition for Inter Partes Review of U.S. Patent No. 8,147,514 Under 35 U.S.C. §§ 311-319 and 37 C.F.R. § 42.100 Et Seq.; filed Oct. 11, 2013; IPR2013-00632; with exhibits, 268 pages.
Declaration of Steve E. Jordan for U.S. Patent No. 8,147,514, IPR 2013-00631, dated Sep. 23, 2013, 38 pages.
Declaration of Steve E. Jordan for U.S. Patent No. 8,147,514, IPR 2013-00632 and IPR 2013-00633, Sep. 23, 2013; (exhibits 1006 & 1009); 61 pages.
Declaration of Steve E. Jordan for U.S. Patent No. 5,921,986, from IPR 2013-00632, dated Sep. 24, 2013 (exhibit 1010); 39 pages.
Declaration of Steve E. Jordan for U.S. Patent No. 5,921,986, from IPR 2013-00633, dated Sep. 24, 2013 (exhibit 1007); 39 pages.
Corrected Petition for Inter Partes Review of U.S. Patent No. 8,147,514 Under 35 U.S.C. §§ 311-319 and 37 C.F.R. § 42.100 Et. Seq.; filed Oct. 11, 2013; IPR2013-00633; with exhibits, 248 pages.
*Bonutti Skeletal Innovations LLC v. Linvatec Corporation and ConMed Corporation*; "Defendants Linvatec and ConMed Corporation's Invalidity Contentions;" With Exhibits; Case No. 6:12-cv-01379; M.D. Florida; Sep. 30, 2013; 2703 pages.
*Bonutti Skeletal Innovations LLC v. Linvatec Corporation and ConMed Corporation*; "Defendants Linvatec and ConMed Corporation's Non-Infringement Contentions;" With Exhibits; Case No. 6:12-cv-01379; M.D. Florida; Sep. 30, 2013; 310 pages.
*Bonutti Skeletal Innovations LLC v. Linvatec Corporation and ConMed Corporation*; "Defendants' Proposed Claim Term Constructions;" With Exhibits; Case No. 6:12-cv-01379; M.D. Florida; Nov. 1, 2013; 53 pages.
*Bonutti Skeletal Innovations LLC v. Linvatec Corporation and ConMed Corporation*; "Defendants' Proposed Terms for Construction;" Case No. 6:12-cv-01379; M.D. Florida; Oct. 10, 2013; 9 pages.
*Bonutti Skeletal Innovations LLC v. Linvatec Corporation and ConMed Corporation*; "Joint Claim Construction Statement;" With Exhibits; Case No. 6:12-cv-01379; M.D. Florida; Nov. 15, 2013; 55 pages.
*Bonutti Skeletal Innovations LLC v. Linvatec Corporation and ConMed Corporation*; "Plaintiff Bonutti Skeletal Innovations LLC's Initial Identification of Disputed Claim Terms;" Case No. 6:12-cv-01379; M.D. Florida; Oct. 10, 2013; 3 pages.
*Bonutti Skeletal Innovations LLC v. Linvatec Corporation and ConMed Corporation*; "Plaintiff Bonutti Skeletal Innovations LLC's Proposed Interpretations of Disputed Claim Terms;" With Exhibits; Case No. 6:12-cv-01379; M.D. Florida; Nov. 1, 2013; 35 pages.
*Bonutti Skeletal Innovations LLC v. Linvatec Corporation and ConMed Corporation*; "Order;" Case No. 6:12-cv-1379-0rl-22TBS; M.D. Florida; Mar. 25, 2014; 22 pages.
*Bonutti Skeletal Innovations LLC v. Arthrex*; "Defendant Arthrex Inc.'s Preliminary Identification of Proposed Claim Terms for Construction by the Court;" Case No. 6:12-cv-01380; M.D. Florida; Mar. 15, 2013; 8 pages.

(56) References Cited

OTHER PUBLICATIONS

*Bonutti Skeletal Innovations LLC v. Arthrex*; "Defendant Arthrex Inc.'s Preliminary Identification of Proposed Claim Terms for Construction by the Court;" Case No. 6:13-cv-00620; M.D. Florida; Oct. 16, 2013; 8 pages.
*Bonutti Skeletal Innovations LLC v. Arthrex*; "Defendant Arthrex, Inc.'s Disclosure of Preliminary Non-Infringement and Invalidity Contentions;" With Exhibits; Case No. 6:13-cv-00620; M.D. Florida; Sep. 23, 2013; 1751 pages.
*Bonutti Skeletal Innovations LLC v. Arthrex*; "Defendant Arthrex, Inc.'s Notice of a First Supplemental Disclosure of Preliminary Invalidity Contentions;" With Exhibits; Case No. 6:13-cv-00620; M.D. Florida; Oct. 24, 2013; 660 pages.
*Bonutti Skeletal Innovations LLC v. Arthrex*; "Defendant Arthrex, Inc.'s Preliminary Constructions of Terms Proposed for Construction by the Court;" Case No. 6:13-cv-01380; M.D. Florida; Mar. 25, 2013; 11 pages.
*Bonutti Skeletal Innovations LLC v. Arthrex*; "Defendant Arthrex, Inc.'s Preliminary Constructions of Terms Proposed for Construction by the Court;" With Exhibit; Case No. 6:12-cv-00620; M.D. Florida; Nov. 1, 2013; 27 pages.
*Bonutti Skeletal Innovations LLC v. Arthrex*; "Defendant Arthrex, Inc.'s Supplemental Claim Construction Statement;" Case No. 6:13-cv-00620; M.D. Florida; Nov. 15, 2013; 9 pages.
*Bonutti Skeletal Innovations LLC v. Arthrex*; "First Amended Complaint with Exhibits" Case No. 6:12-cv-01380; M.D. Florida; Sep. 21, 2012; 259 pages.
*Bonutti Skeletal Innovations LLC v. Arthrex*; "Joint Claim Construction Statement;" Case No. 6:13-cv-00620; M.D. Florida; Nov. 15, 2013; 25 pages.
*Bonutti Skeletal Innovations LLC v. Arthrex*; "Consent Joint Motion for Leave to File Corrected Joint Claim Construction Statement Exhibit;" Case No. 6:13-cv-00620; M.D. Florida; Dec. 12, 2013; 23 pages.
*Bonutti Skeletal Innovations LLC v. Arthrex*; "Notice of Filing Corrected Joint Claim Construction Statement;" Case No. 6:13-cv-00620; M.D. Florida; Dec. 23, 2013; 21 pages.
*Bonutti Skeletal Innovations LLC v. Arthrex*; "Plaintiff Bonutti Skeletal Innovations LLC's Proposed Interpretations of Disputed Claim Terms;" With Exhibits; Case No. 6:13-cv-00620; M.D. Florida; Nov. 1, 2013; 34 pages.
*Bonutti Skeletal Innovations LLC v. Arthrex*; "Plaintiff's Initial Preliminary Identification of Claim Terms and Phrases Potentially Needing Interpretation by the Court;" Case No. 6:13-cv-01380; M.D. Florida; Mar. 15, 2013; 5 pages.
*Bonutti Skeletal Innovation LLC v. Arthrex, Inc.*, "Order," Case No. 6:13-cv-620; M.D. Florida, Mar. 25, 2014, 29 pages.
*Bonutti Skeletal Innovations LLC v. DePuy Mitek LLC, et al.*; "Declaration of Stephen M. Belkoff, Ph.D in Support of Plaintiff Bonutti Skeletal Innovations LLC's Preliminary Claim Construction Brief;" Civil Action No. 1:12-cv-11667; United States District Court District of Massachusetts; Dec. 9, 2013; 49 pages.
*Bonutti Skeletal Innovations LLC v. DePuy Mitek LLC, et al.*; "Defendants' List of Proposed Claim Terms and Phrases for Interpretation;" Civil Action No. 1:12-cv-11667; United States District Court District of Massachusetts; Oct. 3, 2013; 6 pages.
*Bonutti Skeletal Innovations LLC v. DePuy Mitek LLC, et al.*; "Defendants' Preliminary Invalidity Disclosures;" Civil Action No. 1:12-cv-11667; United States District Court District of Massachusetts; Aug. 29, 2013; 73 pages.
*Bonutti Skeletal Innovations LLC v. DePuy Mitek LLC, et al.*; "Defendants' Preliminary Non-Infringement Disclosures;" Civil Action No. 1:12-cv-11667; United States District Court District of Massachusetts; Aug. 29, 2013; 86 pagesq.
*Bonutti Skeletal Innovations LLC v. DePuy Mitek LLC, et al.*; "Defendants' Proposed Claim Constructions;" Civil Action No. 1:12-cv-11667; United States District Court District of Massachusetts; Oct. 10, 2013; 7 pages.
*Bonutti Skeletal Innovations LLC v. DePuy Mitek LLC, et al.*; "Depuy's Opening Claim Construction Brief;" Civil Action No. 1:12-cv-11667; United States District Court District of Massachusetts; Dec. 9, 2013; 35 pages.
*Bonutti Skeletal Innovations LLC v. DePuy Mitek LLC, et al.*; "Joint Appendices A through I;" Civil Action No. 1:12-cv-11667; United States District Court District of Massachusetts; Dec. 9, 2013; 413 pages.
*Bonutti Skeletal Innovations LLC v. DePuy Mitek LLC, et al.*; "Plaintiff Bonutti Skeletal Innovations Llc's Claim Construction Reply Brief;" Civil Action No. 1:12-cv-11667; United States District Court District of Massachusetts; Jan. 16, 2014; 24 pages.
*Bonutti Skeletal Innovations LLC v. DePuy Mitek LLC, et al.*; "Plaintiff Bonutti Skeletal Innovations LLC's List of Proposed Claim Terms and Phrases for Interpretation;" Civil Action No. 1:12-cv-11667; United States District Court District of Massachusetts; Oct. 3, 2013; 4 pages.
*Bonutti Skeletal Innovations LLC v. DePuy Mitek LLC, et al.*; "Plaintiff Bonutti Skeletal Innovations LLC's Preliminary Claim Construction Brief;" Civil Action No. 1:12-cv-11667; United States District Court District of Massachusetts; Dec. 9, 2013; 27 pages.
*Bonutti Skeletal Innovations LLC v. DePuy Mitek LLC, et al.*; "Plaintiff Bonutti Skeletal Innovations LLC's Response to Defendants' Proposed Claim Constructions;" Civil Action No. 1:12-cv-11667; United States District Court District of Massachusetts; Oct. 30, 2013; 14 pages.
*Bonutti Skeletal Innovations LLC v. DePuy Mitek LLC, et al.*; "Plaintiff's Initial Preliminary Infringement Disclosures;" Civil Action No. 1:12-cv-11667; United States District Court District of Massachusetts; May 30, 2013; 8 pages.
*Bonutti Skeletal Innovations LLC v. DePuy Mitek LLC, et al.*; "DePuy's Reply Claim Construction Brief;" Civil Action No. 1:12-cv-11667; United States District Court District of Massachusetts; Jan. 16, 2014; 23 pages.
510k Summary of Safety and Effectiveness; "Mitek Micro Anchor;" Jun. 28, 1996; K962511; 1 page.
Amis, Andrew A.; "Anterior Cruciate Ligament Graft Positioning, Tensioning, and Twisting;" Knee Surgery, Sports Traumatology, Arthroscopy, 6 [Suppl. 1]; 1998; pp. S2-S12.
Amis, Andrew A.; "Anterior Cruciate Ligament Replacement, Knee Stability and the Effects of Implants;" The Journal of Bone and Joint Surgery, 71-B; 1989; pp. 819-824.
Arthrex, Protect your graft, Am J Sports Med, vol. 22, No. 4, Jul.-Aug. 1994.
Ask Oxford projection, compact oxford English dictionary: projection, Mar. 30, 2009.
Ask Oxford projection, compact oxford English dictionary: slit, Mar. 30, 2009.
Barber, F. Alan, et al.; "Suture Anchor Failure Strength—An in Vivo Study;" Arthroscopy: The Journal of Arthroscopic and Related Surgery, vol. 9, No. 6; 1993; pp. 647-652.
Barber, F. Alan; "The Ultimate Strength of Suture Anchors;" Arthroscopy: The Journal of Arthroscopic and Related Surgery, vol. 11, No. 1; Feb. 1995, pp. 21-28.
Barrett, Gene R., et al.; "T-Fix Endoscopic Meniscal Repair: Technique and Approach to Different Types of Tears;" Arthroscopy, vol. 11, No. 2; Apr. 1995; pp. 245-251.
Barrows, Thomas H., et al.; "Synthetic Bioabsorbable Polymers;" High Performance Biomaterials: A Comprehensive Guide to Medical and Pharmaceutical Applications 243 (Michael Szycher ed.); 1991.
Biomet, Stanmore Modular Hip, J. Bone Joint Surg., vol. 76-78: No. Two, Mar. 1994.
Branson, Polymers: Characteristics and Compatibility for Ultrasonic Assembly, Applied Technologies Group, 1971, 4 pages.
Bylski-Austrow, D.I., et al.; "Anterior Cruciate Ligament Replacements: A Mechanical Study of Femoral Attachment Location, Flexion Angle at Tensioning, and Initial Tension;" Journal of Orthopaedic Research, 8; 1990; pp. 522-531.
Cobb, Tyson K., et al.; "Late Correction of Malunited Intercondylar Humeral Fractures Intra-Articular Osteotomy and Tricortical Bone Grafting;" J Bone Joint Surg [Br] 1994; 76-B; pp. 622-626.
Cope, Constantin; "Suture Anchor for Visceral Drainage;" AJR, vol. 146; pp. 160-162; Jan. 1986.

(56) References Cited

OTHER PUBLICATIONS

European Search Report dated Sep. 10, 2012 for EP08732724.3 (046).
Flory, Principles of Polymer Chemistry, 1953, selected pp. 576-595, (cited in IPR 2013-00603, exhibit 1012).
Gao et al., Swelling of Hydroxypropyl Methylcellulose Matrix Tablets, 2. Mechanistic Study of the Influence of Formulation Variables on Matrix Performance and Drug Release, J. of Pharmaceutical Sciences, vol. 85, No. 7, Jul. 1996, p. 732-740.
Gopferich, Mechanisms of polymer degradation and erosion, Biomaterials, 1996, vol. 17, No. 2, p. 103-114.
Grizzi; "Hydrolytic degradation of devices based on poly(DL-lactic acid) size-dependence;" Biomaterials, 1995, vol. 16, No. 4; pp. 305-311.
Grumbine, et al.; "Grappling Suture Fixation Technique;" Clin Podiatr Med Surg. 3(2); 1986; pp. 235-239.
Guide to Ultrasonic Plastics Assembly, Dukane Corporation, Ultrasonic Division Publication, (c) 1995.
Hanna, et al.; "Repair of Distal Tendo Achillis Rupture With the Use of the Mitek Anchor System;" J Am Podiatr Med Assoc, 83(12); Dec. 1993; pp. 663-668.
Hecker, Aaron T., et al.; "Pull-out strength of suture anchors for rotator cuff and Bankart lesion repairs;" The American Journal of Sports Medicine, vol. 21, No. 6; Nov.-Dec. 1993; cover page and pp. 874-879.
Hernigou, PH., et al.; "Proximal Tibial Osteotomy for Osteoarthritis with Varus Deformity A Ten To Thirteen-Year Follow-Up Study;" J Bone Joint Surg, vol. 69-A, No. 3.; Mar. 1987; pp. 332-354.
Intl Prelim Rep on Patentability and Written Opinion for PCT/US10/25263 dated Aug. 30, 2011.
IPER—International Preliminary Report on Patentability, WO/2007/092869, published Aug. 12, 2008 for PCT/US2007/061730.
IPER—International Preliminary Report on Patentability, WO/2008/116203, published Sep. 22, 2009 for PCT/US08/57948.
IPER—International Preliminary Report on Patentability, WO/2009/029908, published Mar. 2, 2010 for PCT/US2008/074941.
IPR—International Publication WO/2007/092869, published Aug. 16, 2007 for PCT/US2007/061730.
IPR—International Publication WO/2008/116203, published Sep. 25, 2008 for PCT/US08/57948.
IPR—International Publication WO/2009/029908, published May 3, 2009 for PCT/US08/79491.
ISR—International Search Report PCT/US2010/025263 completed Apr. 13, 2010.
ISR—International Search Report WO/2007/092869, published Dec. 13, 2007 for PCT/US2007/061730.
ISR—International Search Report WO/2008/116203, published Dec. 24, 2008 for PCT/US08/57948.
ISR—International Search Report, WO/2009/029908, published May 3, 2009 for PCT/US08/029908.
ISR—International Search Report, WO/2009/029908, published Oct. 28, 2008 for PCT/US2008/074941.
Karlsson, J. et al; "Repair of Bankart Lesions With a Suture Anchor in Recurrent Dislocation of the Shoulder;" Scand. J. of Med & Science in Sports, 1995, 5; pp. 170-174.
Kurosaka, Masahiro, et al.; "A Biomechanical Comparison of Different Surgical Techniques of Graft Fixation in Anterior Cruciate Ligament Reconstruction;" The American Journal of Sports Medicine, vol. 15, No. 3; 1987; pp. 225-229.
Lambert, Kenneth L.; "Vascularized Patellar Tendon Graft with Rigid Internal Fixation for Anterior Cruciate Ligament Insufficiency;" Clinical Orthopaedics and Related Research, No. 172; Jan.-Feb. 1983; pp. 85-89.
Ming Li; Structure-Property Relationships in the Case of the Degradation of Massive Aliphatic Poly-(α-Hydroxy Acids) in Aqueous Media (Parts 1-3) Journals of Materials Science: Materials in Medicine 1; 1990; pp. 123-139 and 198-206.
Mosca, Vincent S., et al.; "Calcaneal Lengthening for Valgus Deformity of the Hindfoot: Results In Children Who Had Severe, Symptomatic Flatfoot And Skewfoot;" J Bone Joint Surg, vol. 77-A, No. 4; Apr. 1995; pp. 500-512.
Nabors, Erric D., et al.; "Anterior Cruciate Ligament Graft Tensioning in Full Extension;" The American Journal of Sports Medicine, vol. 23, No. 4; 1995; pp. 488-492.
Obrist, J. et al.; "Bankart Operation With the Mitek Anchor System;" Unfallchirurgie, 17(4); Aug. 1991; pp. 208-212.
Packer, G.J., et al.; "Repair Of Acute Scapho-Lunate Dissociation Facilitated By The 'Tag'* Suture Anchor;" Journal of Hand Surgery (British and European Volume, 1994) 19B: 5; pp. 563-564.
Richmond, John C., et al.; "Modification of the Bankart Reconstruction with a Suture Anchor;" Am J Sports Med, vol. 19, No. 4; 1991; p. 343-346.
Seitz, William, et al.; "Repair of the Tibiofibular Syndesmosis with a Flexible Implant;" Journal of Orthopaedic Trauma, vol. 5, No. 1; 1991; pp. 78-82.
Shelton, W., et al.; "Meniscus Replacement with Bone Anchors: A Surgical Technique;" Arthroscopy: The Journal of Arcioscopic and Related Surgery, 10(3); Jun. 1994; pp. 324-327.
Snyder, SJ; "Evaluation and Treatment of the Rotator Cuff;" Orthop Clin North Am, 24(1); Jan. 1993; pp. 173-192.
Steiner, Mark E., et al.; "Anterior Cruciate Ligament Graft Fixation;" The American Journal of Sports Medicine, vol. 22, No. 2; 1994; pp. 240-247.
Taylor, David E., et al.; "Femoral Bone Plug Recession in Endoscopic Anterior Cruciate Ligament Reconstruction;" Arthoscopy: The Journal of Arthroscopic and Related Surgery, vol. 12, No. 4; Aug. 1996; pp. 513-515.
Textured Surface Technology, Branson Technolog, Branson Technolog TL 4, Branson Ultrasonics Corp., (c) 1992.
Tfix; Acufex just tied the knot between endoscopic surgery and meniscal repair; Am. J. Sports Med., vol. 22, No. 3, May-Jun. 1994; 2 pages.
Translation of FR2696338 with translator's certificate dated Sep. 17, 2013 (cited in IPR 2013-00631, 2013-00632).
Translation of DE9002844.9 with translator's certificate dated Sep. 26, 2013 (cited in IPR 2013-00631, 2013-00632).
Verhaven, E., et al.; "Surgical Treatment of Acute Biceps Tendon Ruptures With a Suture Anchor;" Acta Orthop Belg, 59(4); 1993; pp. 426-429.
Van Heerwaarden, R.J., et al.; "Effect of Pretension in Reconstructions of the Anterior Cruciate Ligament With a Dacron Prosthesis;" Knee Surgery, Sports Traumatology, Arthroscopy, 3; 1996; pp. 202-208.
Westrich, et al.; "Isolated Rupture and Repair of the Popliteus Tendon;" Arthoscopy, 11(5); Oct. 1995; pp. 628-632.
Written Opinion for PCT/US2010/025263 completed Apr. 13, 2010.
Written Opinion WO/2007/092869 dated Aug. 7, 2008 for PCT/US2007/061730.
Written Opinion WO/2008/116203 dated Oct. 23, 2008 for PCT/US08/57948.
Written Opinion WO2009/029908 date Feb. 28, 2010 for PCT/US08/74941.
Yamamoto, Yuhei, et al.; "Application of a Suture Anchor Technique for Flap Fixation to Bone;" Journal of Reconstructive Microsurgery; Jul. 1996, vol. 12, No. 5, pp. 313-315.
Yoshiya, Shinichi, et al.; "Graft Tension in Anterior Cruciate Ligament Reconstruction;" The American Journal of Sports Medicine, vol. 15, No. 5; 1987, pp. 464-470.
Copending U.S. Appl. No. 11/230,020, Final Office Action dated Aug. 2, 2011.
Copending U.S. Appl. No. 12/030,728, Response to Office Action Sep. 21, 2011.
*Bonutti Skeletal Innovations LLC v. DePuy Mitek LLC, et al.*; "Memorandum and Order on Claim Construction;" Civil Action No. 1:12-cv-11667; United States District Court District of Massachusetts; May 2, 2014; 22 pages.
U.S. Appl. No. 14/282,908, May 2014, Bonutti.

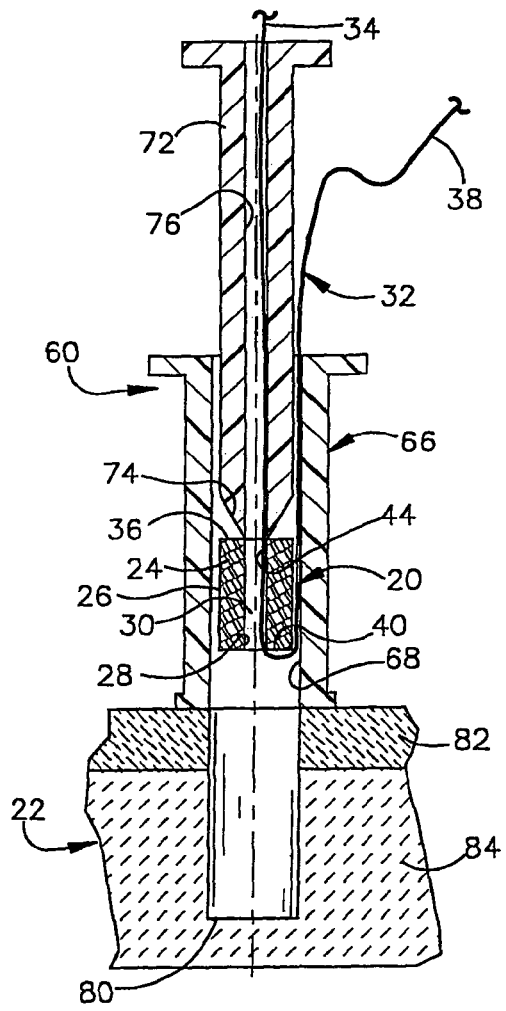
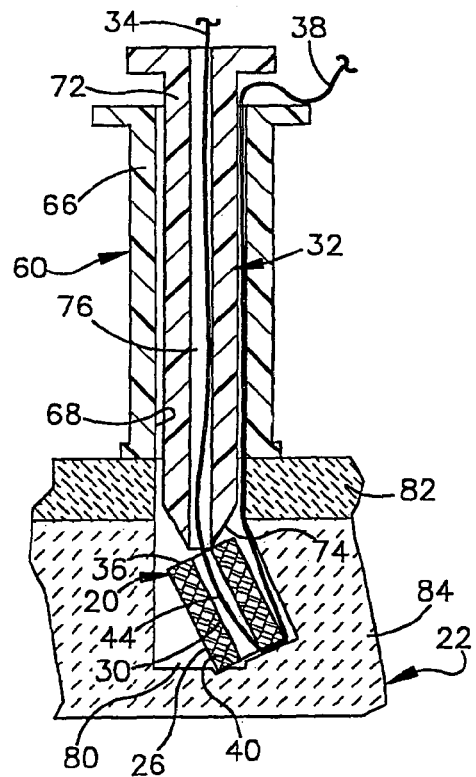
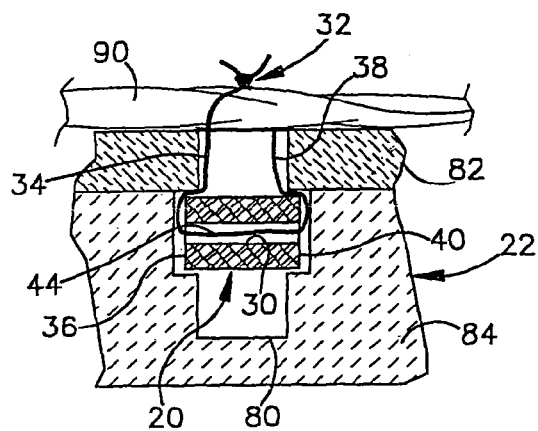

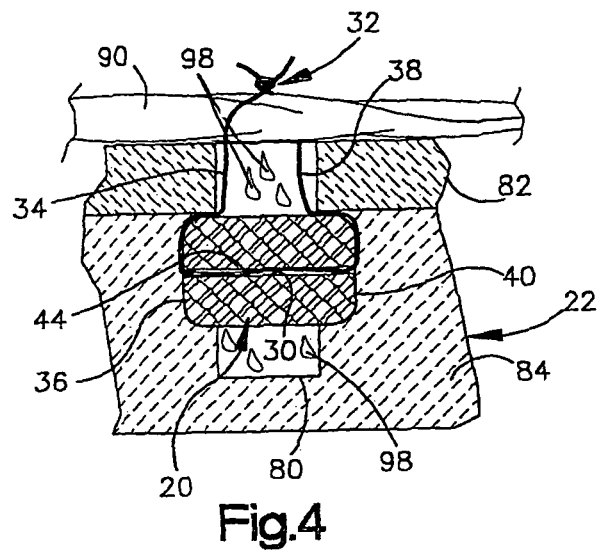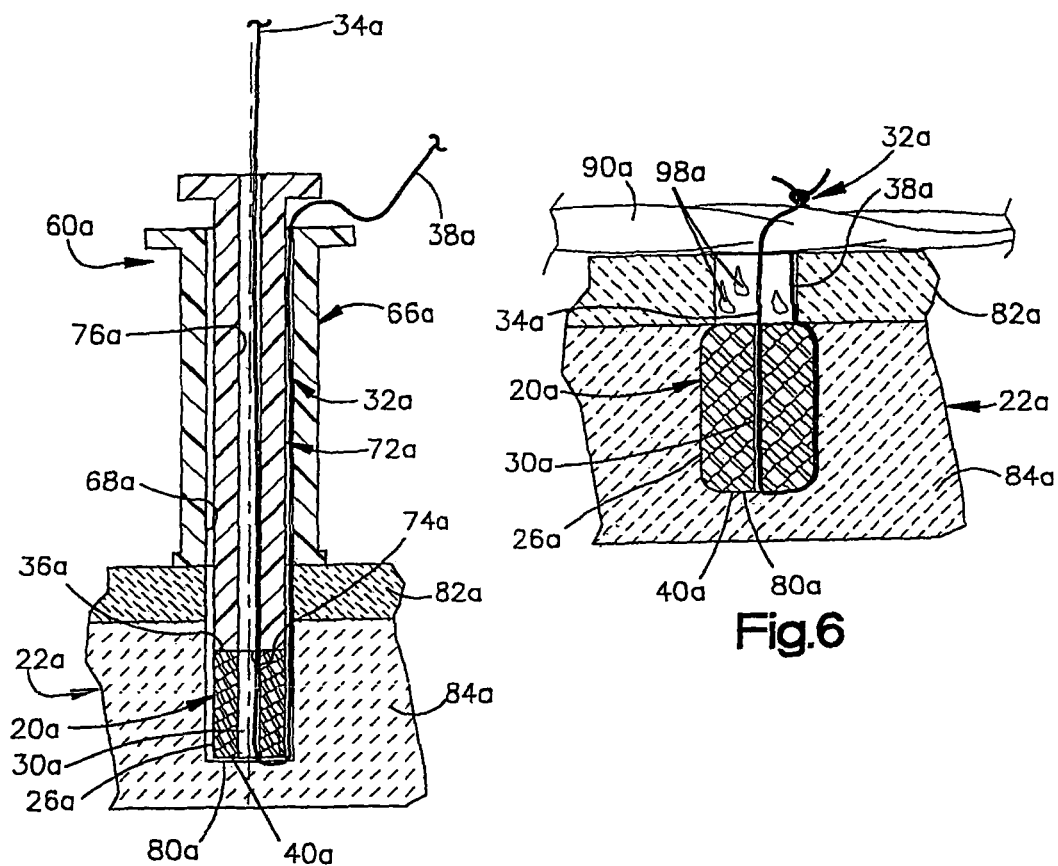

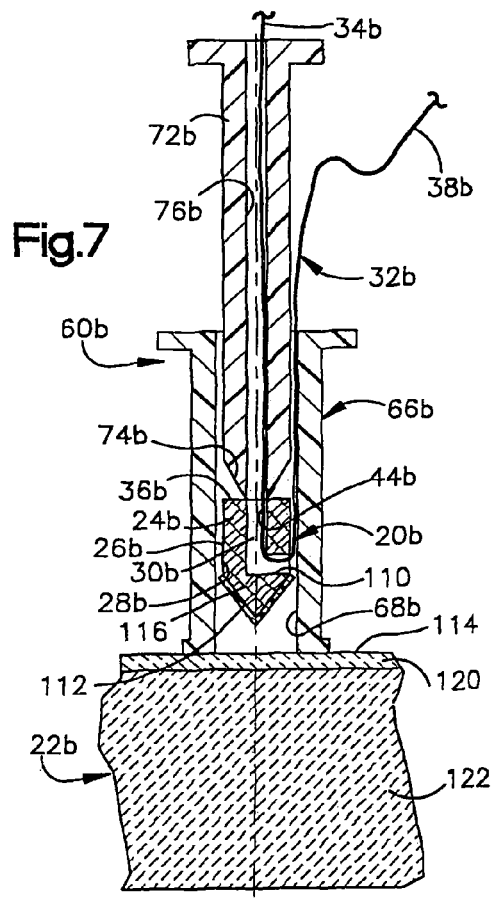
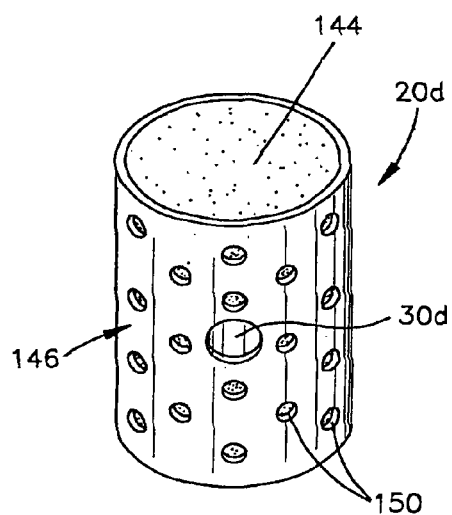
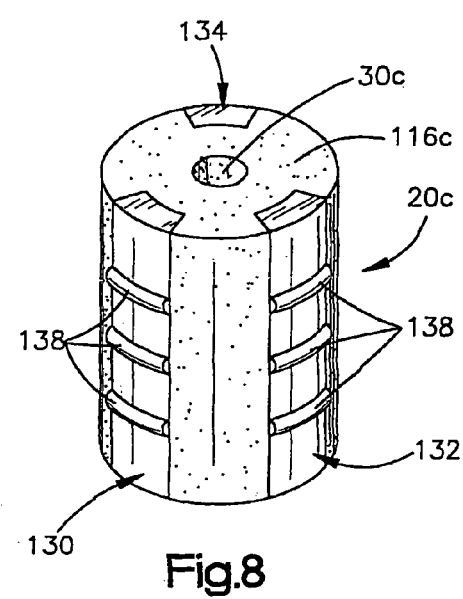
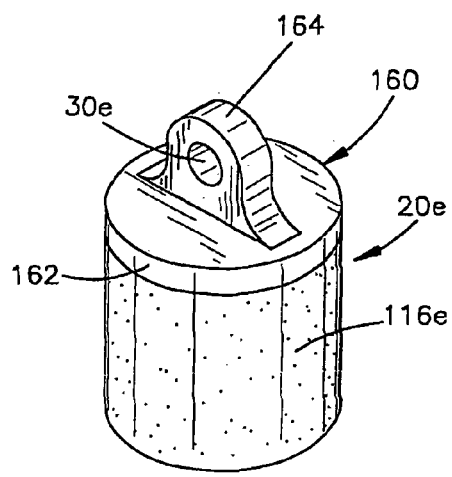

ANCHOR FOR SECURING A SUTURE

RELATED APPLICATIONS

This application is a continuation of U.S. application Ser. No. 11/230,020 filed Sep. 19, 2005; which is a continuation of U.S. application Ser. No. 10/442,353 filed May 21, 2003 (now U.S. Pat. No. 6,955,683). The aforementioned '353 application is itself a continuation of U.S. application Ser. No. 09/703,058 filed Oct. 31, 2000 (now U.S. Pat. No. 6,572,635). The aforementioned '058 application is itself a continuation of U.S. application Ser. No. 09/378,190 filed Aug. 20, 1999 (now U.S. Pat. No. 6,152,949). The aforementioned '190 application is itself a continuation of U.S. application Ser. No. 08/964,167 filed Nov. 4, 1997 (now U.S. Pat. No. 5,980,559). The aforementioned '167 application is itself a divisional of U.S. application Ser. No. 08/699,553 filed Aug. 19, 1996 (now U.S. Pat. No. 5,718,717). The benefit of the earlier filing dates of the aforementioned applications is hereby claimed.

BACKGROUND OF THE INVENTION

The present invention relates to a new and improved suture anchor and more specifically to a suture anchor which is capable of expanding in a patient's body to enable the anchor to withstand relatively large pull-out forces.

Anchors are commonly utilized to retain sutures in a patient's body. The anchors have previously been formed of metal, such as stainless steel or titanium. In addition, anchors have been formed of biodegradable materials. These known anchors have relied upon mechanical interlocks between the body tissue and the anchor to retain the anchor in place against the influence of forces transmitted through the suture to the anchor. It has previously been suggested to construct anchors in the manner disclosed in U.S. Pat. Nos. 5,405,359; 5,403,348; 5,203,787; 5,046,513; and 5,041,129. In addition, an anchor formed of body tissue is disclosed in co-pending application Ser. No. 08/626,393 filed Mar. 29, 1996 filed by Peter M. Bonutti and entitled "Suture Anchor".

SUMMARY OF THE INVENTION

The present invention relates to a new and improved suture anchor which absorbs body liquid. A suture extends from the anchor. The anchor and the suture are inserted into a patient's body. When the anchor is disposed in the patient's body, the anchor expands. The anchor expands by absorbing body liquid and/or by its own natural resilience. As the anchor expands, an improved interlock is obtained between the anchor and the body tissue to enable the anchor to resist relatively large tension forces transmitted through the suture.

The anchor may be formed of a material which absorbs body liquid. Alternatively, the anchor may contain cells which are expanded to absorb body liquid.

The anchor may have a leading end portion which forms an opening in an imperforate body surface. Alternatively, the anchor may be inserted into body tissue through an opening formed in the body tissue by a member other than the anchor. The configuration of the anchor may be changed while the anchor is in the body tissue.

BRIEF DESCRIPTION OF THE DRAWINGS

The foregoing and other features of the invention will become more apparent upon a consideration of the following description taken in connection with the accompanying drawings, wherein:

FIG. 1 is a schematic illustration depicting the manner in which an anchor is inserted into a patient's body with a suture extending into the anchor;

FIG. 2 is a schematic illustration depicting the manner in which the anchor of FIG. 1 is pivoted in the patient's body;

FIG. 3 is a schematic illustration depicting the manner in which the patient's body tissue is secured with the anchor immediately after the anchor has been inserted into the patient's body;

FIG. 4 is a schematic illustration, generally similar to FIG. 3, illustrating the manner in which the anchor expands by absorbing body liquid after the anchor has been inserted into the patient's body;

FIG. 5 is a schematic illustration depicting another manner in which the anchor of FIG. 1 may be inserted into a patient's body;

FIG. 6 is a schematic illustration depicting the manner in which the anchor of FIG. 5 expands in the patient's body by absorbing body liquid;

FIG. 7 is a schematic illustration, generally similar to FIG. 1, illustrating the manner in which a second embodiment of the anchor may be inserted into a patient's body through an imperforate surface on body tissue;

FIG. 8 is a schematic pictorial illustration of a third embodiment of the anchor having a portion which absorbs body liquid and a portion which does not absorb body liquid and has projections to engage body tissue;

FIG. 9 is a schematic pictorial illustration of a fourth embodiment of the anchor having a core which absorbs body liquid and a casing formed of an elastic material which does not absorb body liquid;

FIG. 10 is a pictorial schematic illustration of a fifth embodiment of the anchor having an end portion with a suture receiving opening formed in material which does not absorb body liquid and is connected with a main portion which absorbs body liquid;

DESCRIPTION OF SPECIFIC PREFERRED EMBODIMENTS OF THE INVENTION

General Description

Figure 11:
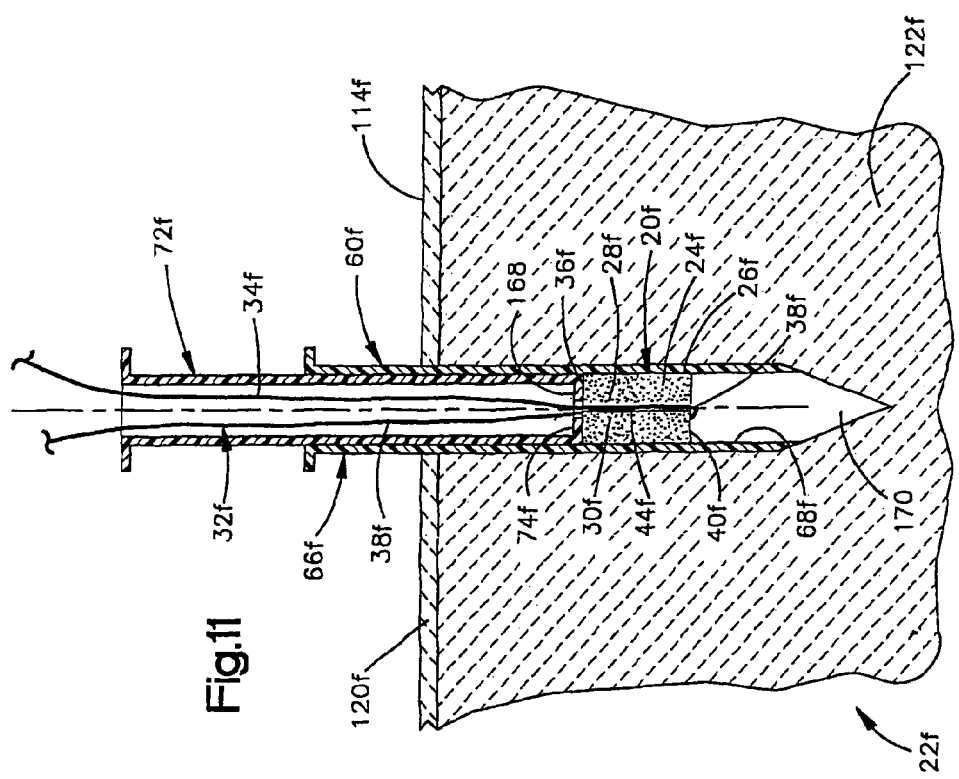
FIG. 11 is a schematic illustration of a an apparatus for inserting an anchor having cells which are collapsed before the anchor is moved into a patient's body.

Suture anchors have previously been utilized to retain sutures in either hard or soft tissue in a human patient's body. The suture anchors have previously been formed of metal, biodegradable materials, and other materials. These known suture anchors have been retained in the patient's body by changing the orientation of the anchor relative to the patient's body once it has been inserted into the patient's body. Alternatively, known anchors have been retained in the patient's body by a mechanical interlock formed with the material of the patient's body by barbs or other projections.

In accordance with one of the features of the present invention, sutures may be retained in a patient's body by anchors which are at least partially formed of material which absorbs body liquid when exposed to the body liquid. The material expands as it absorbs the liquid in the patient's body. As the anchor expands, an improved interlock is formed between the anchor and body tissue of the patient's body. The improved interlock enables relatively large forces to be transmitted through a suture to the anchor.

In accordance with another of the features of the present invention, sutures may be retained in a patient's body by anchors which are formed of material which expands under the influence of its own natural resilience. As the material expands, cells are expanded from a collapsed condition. As the cells expand, the anchor absorbs body liquid by at least partially filling the cells with body liquid. As the anchor expands, an improved interlock is formed between the anchor and tissue of the patient's body. If desired, the material which forms the cells could also absorb body liquid.

In accordance with another feature of the invention, the anchor could be inserted into a patient's body through an imperforate surface on body tissue. This may be done by forming an opening in the body tissue with a leading end portion of the anchor. Alternatively, the opening could be formed by one or more members other than the anchor. Once the anchor has entered the patient's body the configuration of the anchor may be changed under the combined influence of force transmitted to the anchor through the suture and force applied against the outer surface of the anchor by body tissue.

Suture Anchor Formed of Material which Absorbs Body Liquid

A suture anchor 20 (FIG. 1) is formed of a material which absorbs body liquid when the anchor is exposed to body liquid. As the material of the anchor 20 absorbs body liquid, the anchor expands from the initial volume of FIGS. 1-3 to the expanded volume of FIG. 4. As the material of the anchor 20 absorbs body liquid and expands, the volume of the anchor increases and an improved mechanical interlock is formed between the anchor and body tissue in which the anchor has been inserted. The improved interlock enables the anchor 20 to resist large tension forces in a suture 32 without pulling out of body tissue 22.

It is contemplated that the anchor 20 could be completely formed of material which absorbs body liquid. Alternatively, the anchor could be partially formed of material which absorbs body liquid and partially formed of material which does not absorb body liquid. The material which does not absorb body liquid may be provided with projections which are forced into the body upon expansion of the material which absorbs body liquid. This would result in at least two different interlocks being obtained between the anchor and the body tissue, that is, an interlock due to expansion of the material which absorbs body liquid and an interlock due to engagement of projections on the material which does not absorb body liquid with the body tissue.

The suture anchor 20 is entirely formed of material which absorbs body liquid. In one specific instance, the suture anchor 20 was formed of a polymeric material which absorbs body liquid. The polymeric material may be either a copolymer or a dipolymer. The polymeric material may be hydrophilic. The polymeric material may be cellulose, petroylglutamic acid, high purity carboxymethylcellulose, a collagen, or polylactide. It is believed that a ceramic as found in hydroxyapatite composites with polyethylene, polylactide or polyhydroxybutyrate may be utilized to form the anchor 20. Of course, the suture anchor 20 could be formed of other known materials which absorb body liquid.

It is theorized that the hydrophilic material forming the anchor 20 attracts body liquid under the influence of molecular attraction and establishes molecular linkages with the body liquid. The material forming the anchor 20 is body liquid permeable. The body liquid enters minute cavities in the porous material forming the anchor 20 under the influence of capillary action. The attractive forces between molecules of the body liquid and molecules of the material forming the anchor 20 holds the body liquid in the minute cavities in the material forming the anchor.

In the embodiment of the invention illustrated in FIGS. 1-3, the suture anchor 20 has a tubular cylindrical configuration. The suture anchor 20 has a tubular wall 24 formed of material which absorbs body liquid. The tubular wall 24 has a cylindrical outer side surface 26 which is coaxial with a cylindrical inner side surface 28. The cylindrical inner side surface 28 forms a cylindrical passage 30 which extends axially through the center of the suture anchor 20.

The wall 24 of the suture anchor 20 is formed as one piece of a porous hydrophilic polymer which absorbs body liquid. Although it is preferred to form the anchor 20 with a cylindrical configuration, the anchor may be shaped or ground to any one of many different axially tapering or flaring configurations, such as those disclosed in U.S. Pat. No. 5,403,348. It is believed that it may be preferred to form the anchor 20 with either a cylindrical configuration or a polygonal configuration.

Although it is contemplated that the tubular cylindrical suture anchor 20 could be of many different sizes, it is believed that the suture anchor may preferably have a length or axial extent of between 2 and 4 millimeters. The cylindrical outer side surface 26 of the suture anchor 20 may have a diameter of between 1 and 2 millimeters. The cylindrical inner side surface 28 of the passage 30 in the anchor 20 may have a diameter of ½ to 1 millimeter. Of course, the suture anchor 20 could be formed with many different dimensions and/or shapes if desired.

A suture 32 is inserted into the passage 30 in the suture anchor 20. The suture 32 includes a portion or leg 34 which extends away from a flat annular trailing end surface 36 of the anchor 20. In addition, the suture 32 has a second portion or leg 38 which extends across a flat annular leading end surface 40 of the anchor 20. The leg 38 of the suture 32 extends along the cylindrical outer side surface 26 of the anchor 20 to a location adjacent to and spaced from the leg portion 34 of the suture 32. A relatively short portion 44 of the suture 32 interconnects the leg portions 34 and 38 and is disposed in the passage 30 in the suture anchor 20.

An inserter assembly 60 is used to position the suture anchor 20 and a portion of the suture 32 in a patient's body tissue 22. The inserter assembly 60 includes a cylindrical tubular outer sleeve 66 having a cylindrical central passage 68 in which the anchor 20 is disposed. The inserter 60 also includes a cylindrical tubular inner sleeve 72 which is telescopically received in the outer sleeve 66. The tubular inner sleeve 72 has a conical tapered leading end portion 74 which engages an annular trailing end surface 36 of the anchor 20.

The leg or portion 34 of the suture 32 extends through a cylindrical passage 76 in the inner sleeve 72. The leg or portion 38 of the suture 32 extends through the central passage 68 in the outer sleeve 66 along a path which extends between the inner and outer sleeves. The leg or portion 38 of the suture 32 could extend along the outside of the outer sleeve 66. If desired, one of the legs or portions 34 or 38 of the suture could be omitted. If this was done, the suture 32 could be tied or otherwise secured to the anchor 20.

It is contemplated that the anchor 20 may be inserted into a human patient's body at many different locations. The anchor 20 may be inserted into either hard or soft tissue. In the situation illustrated schematically in FIG. 1, the anchor 20 is being inserted into bone tissue 22 in a patient's body. A cylindrical recess 80 is formed in the bone tissue 22 of the patient's body by drilling or other methods. The recess 80 extends through a hard compact outer layer 82 of the patients bone tissue 22 into the relatively porous inner or cancellous tissue 84.

To insert the anchor 20 in the patient's body tissue 22, the cylindrical inner sleeve 72 is moved axially downward (as viewed in FIG. 1) to apply force against a relatively small area on the annular trailing end surface 36 of the anchor 20. Once the anchor 20 has been pushed into the recess 80 by axial movement of the inner sleeve 72 relative to the outer sleeve 66, the leg 38 of the suture 32 is tensioned to apply force against an annular leading end surface 40 of the anchor 20. At the same time, the bevelled leading end 74 of the inner sleeve 72 is pressed against the trailing end-surface 36 of the anchor.

This results in the application of a counterclockwise (as viewed in FIGS. 1 and 2) torque to the anchor 20. This torque causes the anchor 20 to pivot through the orientation shown in FIG. 2 to the orientation shown in FIG. 3. Once the anchor 20 has been pivoted to the orientation shown in FIG. 3, by tensioning the suture 32 and applying force against the anchor with the leading end portion 74 of the inner sleeve 72, the anchor 20 engages the hard compact outer layer 82 of the patient's bone tissue to hold the anchor in the recess 80. Thus, a solid initial interlock is obtained between the anchor 20 and body tissue 22.

The suture 32 is then tensioned to secure a member, such as body tissue 90, in place. The member or body tissue 90 may be soft tissue, or a ligament, or a tendon, or other body tissue. If desired, the suture 32 may be used to secure other members, such as an implant or splint, in place relative to the patient's body tissue 22. The suture is tensioned to transmit force between the anchor 20 and a member to be held in place.

One specific known inserter assembly 60 and method of inserting a suture anchor 20 into a patient's body tissue has been illustrated in FIGS. 1-3. This specific inserter assembly and the method of inserting the anchor 20 are the same as is disclosed in U.S. Pat. No. 5,403,348 issued Apr. 4, 1995 and entitled "Suture Anchor". However, it is contemplated that many different known types of inserter assemblies could be utilized to install the suture anchor 20 with many different methods in a patient's body tissue. For example, the inserter assembly and method disclosed in U.S. Pat. No. 5,464,426 issued Nov. 7, 1995 and entitled "Method of Closing Discontinuity in Tissue" could be utilized if desired. Of course, other known apparatus and methods could also be utilized if desired.

In accordance with a feature of the invention, the suture anchor 20 absorbs body liquid and expands once the suture anchor has been inserted into the body tissue 22. The expansion of the suture anchor 20 improves the initial interlock between the anchor and body tissue 22. The initial interlock between the anchor 20 and body tissue 22 is obtained by pivoting the anchor in the body tissue to the orientation shown in FIG. 3. The improved interlock is obtained by expanding the anchor 20, as shown in FIG. 4. The improved interlock allows relatively large tension forces to be transmitted through the suture 32 between the anchor 20 and a member to be held in place by the suture.

The suture anchor 20 expands in all directions, from the initial size illustrated in FIG. 3 to a relatively large expanded size illustrated in FIG. 4, shortly after the suture anchor has been inserted into the body tissue 22. After the suture anchor 20 has been inserted into the body tissue 22, the suture anchor is exposed to body liquids, indicated schematically at 98 in FIG. 4. The body liquids 98 are drawn into the suture anchor 20 due to the affinity of the polymeric material forming the suture anchor 20 for body liquids.

As the body liquids 98 are drawn into the suture anchor 20, the anchor expands in a substantially uniform manner in all directions. Thus, the anchor 20 swells both radially and axially. Substantially uniform expansion of the entire outer side surface area of the suture anchor 20 occurs as body liquids 98 are absorbed by the anchor. The extent of expansion of the suture anchor 20 will depend upon the specific characteristics of the material from which the suture anchor is formed and may vary between 10 and 50 percent by volume. Of course, the extent of expansion of the anchor 20 will be a function of the force applied against the outer side surface of the anchor by the body tissue 22.

As the suture anchor 20 swells, the size of the anchor 20 increases. As the size of the anchor 20 increases, the outer side surface of the anchor presses both axially and radially outward against the body tissue 22. As the anchor 20 expands and presses against the body tissue, the body tissue is displaced by the anchor. Thus, the outer side surface of the anchor 20 applies force against the body tissue 22 and moves the body tissue to make room for the anchor as the anchor expands. If the anchor 20 encounters a localized area of high resistance to expansion in the body tissue, the anchor will expand around the localized area and may even shift in the body tissue 22.

The expansion of the anchor 20 as it absorbs the body liquids 98 results in an increasing mechanical interlocking action between the anchor 20 and the body tissue 22. There is an initial mechanical interlock between the anchor 20 and the body tissue 22 when the anchor has its original or initial size (FIG. 3). As body liquids 98 are absorbed by the suture anchor 20 and the volume of the anchor increases, the anchor expands to improve the mechanical interlock between the anchor and the body tissue 22. The improved interlock between the anchor 20 and body tissue 22 allows relatively large tension forces to be transmitted through the suture 32 without pulling the anchor out of the body tissue.

Installation—Second Procedure

In the embodiment of the invention illustrated in FIGS. 1-4, the anchor 20 was pivoted from the orientation shown in FIG. 1 through the orientation shown in FIG. 2 to the orientation shown in FIG. 3 to obtain an initial mechanical interlock between the anchor and body tissue 22. In the embodiment of the invention illustrated in FIGS. 5 and 6, the anchor is not pivoted from its initial orientation to obtain an initial mechanical interlock. The anchor is merely positioned in the body tissue and expanded in all directions by absorbing body liquid. The expansion of the anchor results in the formation of an interlock between the anchor and the body tissue. Since the embodiment of the invention illustrated in FIGS. 5 and 6 is generally similar to the embodiment of the invention illustrated in FIGS. 1-4, similar numerals will be utilized to designate similar components, the suffix letter "a" being associated with the numerals of FIGS. 5 and 6 in order to avoid confusion.

The suture anchor 20a has the same construction and is formed of the same hydrophilic polymeric material as the suture anchor 20 of FIGS. 1-3. The suture anchor 20a (FIG. 5) has a cylindrical tubular configuration. The suture anchor 20a has a cylindrical outer side surface 26a. A cylindrical central passage 30a extends through the suture anchor 20a between opposite annular end surfaces 36a and 40a of the suture anchor 20a.

A suture 32a has a leg 34a which extends through a passage 76a formed in an inner sleeve 72a. A second leg 38a of the suture 32a extends through a central passage 68a and a tubular outer sleeve 66a. The leg 38a of the suture 32a extends between a cylindrical inner side surface 68a of the inner sleeve 72a and a cylindrical inner side surface of the outer sleeve 66a.

It is contemplated that the anchor 20a maybe inserted into a patient's body at many different locations. The anchor 20a may be inserted into either hard or soft tissue. In the situation illustrated schematically in FIG. 5, the anchor is being inserted-into bone tissue 22a in a patient's body with the inserter assembly 60a. A recess 80a is formed in the bone tissue 20a of the human patient's body by drilling or other methods. The cylindrical recess 80a extends through the hard compact outer layer 82a of the patient's bone tissue 20a into the relatively porous inner or cancellous tissue 84a.

To insert the anchor 20a in the patient's body tissue 22a, the inner sleeve 72a is moved axially downward (as viewed in FIG. 5) to apply force against the trailing end surface 36a of the anchor 20a. In this embodiment of the inserter assembly 60a, the inner sleeve 72a has a cylindrical leading end portion 74a which applies a substantially uniform force over substantially the entire flat annular trailing end surface 36a of the anchor 20a. Therefore, the anchor 20a is not pivoted but is merely moved straight into the recess 80a.

Once the anchor 20a has been positioned in the recess 80a, the anchor absorbs body liquid 98a and increases in volume as the liquid is absorbed. This results in the anchor expanding in all directions from the initial size of FIG. 5 to a relatively large expanded size illustrated in FIG. 6. As the anchor 20a expands, its size increases by 10 to 50 percent by volume.

The anchor 20a is porous and is formed of a hydrophilic material. The body liquid 98a is drawn into openings in the porous material of the anchor 20a by the affinity of the porous material forming the anchor for the body liquid. The attractive forces between the material forming the anchor 20a and the body liquid holds the body liquid in the anchor.

As the anchor 20a expands from the initial size, the outer surfaces on the anchor press radially and axially against the body tissue 22a. Substantially uniform expansion of the anchor 20a forms a secure mechanical interlock with the body tissue. This interlock enables tension forces to be transmitted through the suture 32a between the anchor 20a and a member, such as the body tissue 90a.

As the anchor 20a expands radially outward, the cancellous tissue 84a is compressed and the size of the portion of the recess 80a in the cancellous tissue 84a is increased. As this happens, the diameter of the cylindrical anchor 20a increases from a diameter which is just slightly less than the size of the portion of the recess 80a which extends through the hard compact outer layer 82a of the bone tissue 22a to a diameter which is greater than the diameter of the portion of the recess 80a extending through the hard compact outer layer 82a of bone tissue. This results in the anchor 20a being locked in place in the body tissue 22a.

The suture 32a can then be used to secure a member 90a in place in the manner illustrated schematically in FIG. 6. The member 90a may be soft body tissue, or a ligament, or a tendon, or other body tissue. If desired, the suture 32a may be used to secure an implant or splint in place relative to the patient's body 22a. The interlock between the anchor 20a and body tissue 22a enables substantial tension force to be transmitted through the suture 32a without pulling the anchor out of the body tissue.

The expansion of the anchor 20a has been schematically illustrated in FIG. 6 as being uniform in all directions. This will be the case when the body tissue 22a applies uniform forces against all sides of the anchor 20a. However, the body tissue 22a may provide nonuniform resistance to expansion of the anchor 20a. When this occurs, the anchor 20a may shift in the body tissue 22a under the influence of forces applied against the body tissue as the anchor expands. In addition or alternatively, the anchor 20a may expand in a nonuniform manner.

Anchor—Second Embodiment

In the embodiment of the invention illustrated in FIGS. 1-4, the anchor 20 has a generally cylindrical configuration and is formed entirely of a hydrophilic polymeric material which absorbs body liquid. The anchor illustrated in FIGS. 1-4, due to its relatively blunt leading end portion, is particularly well adapted for positioning in preformed recesses in body tissue. In the embodiment of the anchor illustrated in FIG. 7, the anchor has a sharp or pointed leading end portion to facilitate forming an opening in imperforate body tissue. Since the embodiment of the invention illustrated in FIG. 7 is generally similar to the embodiment of the invention illustrated in FIGS. 1-4, similar numerals will be utilized to designate similar components, the suffix letter "b" being associated with the numerals of FIG. 7 to avoid confusion.

The tubular cylindrical suture anchor 20b has a generally cylindrical outer side surface 26b which is coaxial with a cylindrical inner side surface 28b. The cylindrical inner side surface 28b forms a portion of a passage 30b which extends through the anchor 20b. In addition to the main portion of the passage 30b formed by the cylindrical side surface 28b, a second cylindrical side surface 110 has a central axis which extends perpendicular to the central axis of the cylindrical side surface 28b. The cylindrical side surface 110 intersects the cylindrical side surface 28b and extends radially outward from the cylindrical side surface 28b. The cylindrical side surfaces 28b and 110 cooperate to form the passage 30b with a generally L-shaped configuration.

A suture 32b is inserted into the passage 30b in the suture anchor 20b. The suture 32b includes a portion or leg 34b which extends away from a flat annular trailing end surface 36b of the anchor 20b. In addition, the suture 32b has a second portion or leg 38b which extends along the cylindrical outer side surface 26b of the anchor 20b and along the cylindrical inner side surface 68b of the outer sleeve 66b. A relatively short portion 44b of the suture 32b interconnects the leg portions 34b and 38b and is disposed in the passage 30b in the suture anchor 20b.

An inserter assembly 60b is used to position the suture anchor 20b and a portion of the suture 32b in a patient's body tissue 22b. The inserter assembly 60b includes a generally cylindrical tubular outer sleeve 66b having a central passage 68b in which the anchor 20b is disposed. The inserter 60b also includes a tubular inner sleeve 72b which is telescopically received in the outer sleeve 66b. The tubular inner sleeve 72b has a conical tapered leading end portion 74b which engages the trailing end surface 36b of the anchor 20b.

In accordance with a feature of the embodiment of the invention illustrated in FIG. 7, the anchor 20b has a leading end portion 112 with a generally conical configuration. The leading end portion 112 of the anchor 20b is adapted to form an opening in an imperforate outer side surface 114 of the patient's body tissue 22b. In addition, the leading end portion 112 of the anchor 20b facilitates moving the anchor into the body tissue 22b under the influence of force applied against the trailing end surface 36b of the anchor 20b by the tubular inner sleeve 72b. The conical leading end portion 112 of the anchor 20b is formed by a conical layer of a relatively hard polymeric material. The polymeric material forming the leading end portion 112 may be biodegradable if desired.

In addition, the anchor 20b has a cylindrical body portion or wall 116 which is disposed in a coaxial relationship with the leading end portion 112. The cylindrical body portion 116 is formed of a hydrophilic polymeric material which absorbs body liquid when exposed to the body liquid. The cylindrical body portion 116 is formed of the same material as the anchor 20 of FIGS. 1-4. As the body portion 116 of the anchor 20b absorbs body liquid, the body portion of the anchor expands radially and axially to interlock with the body tissue 22b. The leading end portion 112 is formed of a rigid polymeric material which does not absorb body liquid. The leading end portion 74b of the tubular inner sleeve 72b is tapered so that it applies force against the trailing end surface 36b of the anchor 20b at a relatively small area on the trailing end surface. The concentrated application of force to the trailing end surface 36b of the anchor 20b facilitates pivoting movement of the anchor in the body tissue 22b upon tensioning of the leg 38b of the suture 32b.

Assuming the anchor 20b is to be moved into body tissue 22b disposed beneath a layer 120 of skin, force is applied against the tubular inner sleeve 72b to force the pointed leading end portion 112 of the anchor against the imperforate outer side surface 114 of the skin 120. This force causes the anchor 20b to pierce the skin 120 and enter soft body tissue 122 disposed beneath the skin. Once the anchor 20b has been moved completely beneath the skin 120 into the soft body tissue 122, the leg 38b of the suture 32b is tensioned. This results in the application of torque to the anchor 20b tending to rotate or pivot the anchor in a counterclockwise direction from the orientation shown in FIG. 7 to a generally horizontal orientation, corresponding to the orientation of the anchor illustrated in FIG. 3. At this time, the longitudinal central axis of the anchor will be generally parallel to the skin 120.

Once the anchor 20b has been moved into the body tissue 122 and pivoted in the manner previously explained, the body portion 116 of the anchor will absorb body liquid, such as blood or other fluids. As the hydrophilic body portion 116 of the anchor 20b absorbs body liquids, the body portion expands in all directions and presses against the body tissue 122. As the anchor expands, body tissue is displaced and the mechanical interlock with the anchor 20b is enhanced.

Thus, the anchor 20b is mechanically interlocked with the body tissue 122 by both pivotal movement of the anchor to a sidewise orientation and expansion of the anchor as it absorbs body liquids. The improved interlock obtained by expanding the anchor 20b enables relatively large tension forces to be transmitted between a member (not shown) and the anchor 20b through the suture 32b.

Anchor—Third Embodiment

In the embodiment of the anchor illustrated in FIGS. 1-4, the anchor is formed entirely of material which absorbs body liquid when it is exposed to the body liquid. In the embodiment of the anchor illustrated in FIG. 8, a portion of the anchor is formed of material which absorbs body liquid and another portion of the anchor is formed of material which does not absorb body liquid. The material which does not absorb body liquid has projections which engage body tissue to enhance an interlock between the anchor and the body tissue. Since the embodiment of the invention illustrated in FIG. 8 is generally similar to the embodiment of the invention illustrated in FIGS. 1-4, similar numerals will be utilized to designate similar components, the suffix letter "c" being associated with the numerals of FIG. 8 in order to avoid confusion.

An anchor 20c (FIG. 8) has a tubular cylindrical configuration. A suture (not shown) extends through a central passage 30c in the anchor 20c in the same manner as illustrated in FIG. 1 for the anchor 20.

In accordance with a feature of this embodiment of the invention, the anchor 20c (FIG. 8) has a body portion 116c which is formed of a hydrophilic polymeric material which absorbs body liquid when exposed to the body liquid. In addition, the anchor 20c includes a plurality of identical retaining portions 130, 132 and 134. The retaining portions 130, 132 and 134 are formed of a relatively hard polymeric material which does not absorb body liquid. The retaining portions 130, 132 and 134 may be biodegradable if desired.

In the illustrated embodiment of the invention, the retaining portions 130, 132 and 134 and a plurality of ribs or projections 138 which extend outward from the retaining portion. When the anchor 20c is positioned in body tissue in the manner previously explained in conjunction with the embodiments of the invention illustrated in FIGS. 1-4, the body portion 116c absorbs body liquid. When this occurs, the body portion 116c of the anchor 20c expands radially and axially outward to enhance the mechanical interlock with the body tissue.

As the body portion 116c of the anchor 20c expands, the retaining portions 130, 132 and 134 are moved radially outward away from the central axis of the anchor 20c. This presses the ribs 138 on the retaining portions 130, 132 and 134 into the body tissue to further enhance the mechanical interlock between the anchor and the body tissue. Although the ribs 138 have been shown in FIG. 8 as having a generally arcuate configuration and a generally smooth outer side surface, it is contemplated that the ribs could have barbs or other projections which would impale the body tissue as the body portion 116c of the anchor 20c absorbs body liquid and expands. Of course, this would further enhance the mechanical interlock between the anchor 20c and the body tissue.

In the embodiment of the anchor 20c illustrated in FIG. 8, the anchor has a generally flat annular leading end portion. However, it is contemplated that the anchor 20c could be provided with a conical leading end portion, similar to the conical leading end portion 112 on the anchor 20b of FIG. 7. If the anchor 20c were to be provided with a conical leading end portion, it is contemplated that the retaining portions 130, 132 and 134 could be extended in an axial direction to form the conical leading end portion as three separate segments. As the body portion 116c of the anchor 20c absorbs body liquid and expands, the retaining portions 130, 132 and 134 would move radially outward away from each other and the leading end portion of the anchor would expand.

A relatively strong interlock is obtained between the anchor 20c and body tissue. This interlock is obtained by changing the orientation of the anchor 20c relative to the body tissue, in the manner illustrated for the anchor 20 in FIG. 2. In addition, the interlock is obtained by expansion of the anchor 20c as the body portion 116c absorbs body liquid. The interlock is also obtained by engagement of the ribs 138 with body tissue. The result is a strong interlock which enables the anchor 20c to resist very large tension forces transmitted to the anchor through a suture.

Anchor—Fourth Embodiment

In the embodiment of the anchor 20 illustrated in FIGS. 1-4, the anchor is formed entirely of material which expands when it is exposed to body liquid. In the embodiment of the invention illustrated in FIG. 9, the anchor is formed by a core of material which expands upon being exposed to body liquid and an elastic jacket which encloses the core. Since the embodiment of the invention illustrated in FIG. 9 is generally similar to the embodiment of the invention illustrated in FIGS. 1-4, similar numerals will be utilized to designate similar components, the suffix letter "d" being associated with the numerals of FIG. 9 in order to avoid confusion.

An anchor 20d (FIG. 9) has a cylindrical configuration. The anchor 20d includes a cylindrical core 144 which is enclosed by a tubular cylindrical jacket 146. A passage 30d extends through both the core 144 and the jacket 146. The passage 30*d* extends diametrically through the core 144 and the jacket 146 and has a cylindrical configuration. A suture (not shown) is positioned in the passage 30*d*. The suture may be tied off at one end of the passage or may extend through the passage so that legs of the suture extend along opposite sides of the jacket 146.

The jacket 146 is provided with a plurality of circular openings 150 which extend through the jacket. The openings 150 enable body liquid to pass through the jacket into the core 144. The jacket 146 is formed of an elastic polymeric material which is easily stretched. The core 144 is formed of a material which absorbs body liquid upon being exposed to the body liquid. In one specific embodiment of the suture anchor 20*d*, the core 144 was formed of a hydrophilic polymeric material which is the same as the material forming the anchor 20 of FIGS. 1-4.

When the anchor 20*d* is inserted into body tissue, in the manner illustrated schematically in either FIGS. 1-3 or 5 and 6, the entire anchor 20*d* is exposed to body liquid. The body liquid passes through the openings 150 and is absorbed by the core 144. As the core 144 absorbs body liquid, the core expands and stretches the jacket 146.

Although the anchor 20*d* has been shown as having a generally cylindrical configuration with flat annular end surfaces, it is contemplated that the anchor could be provided with a conical leading end portion, similar to the conical leading end portion 112 of the anchor 20*b* of FIG. 7. The conical leading end portion could be formed either as a portion of the jacket 46 or separately from the jacket. It is believed that it may be preferred to form a conical leading end portion for the anchor 20*d* separately from the jacket 146 to enable the leading end portion to be formed of a hard material which is not readily stretched and which is capable of piercing an imperforate surface of body tissue.

In the illustrated embodiment of the invention, the jacket 146 is formed of a material which is resiliently stretched when the core 144 absorbs body liquid and expands. It is contemplated that the size of the jacket 146 could be increased in other ways to accommodate expansion of the core. For example, releasable tucks could be formed in the jacket. Upon expansion of the core, stitches or other devices holding the tucks would be released under the influence of force applied against the jacket by the core.

Anchor—Fifth Embodiment

The anchors illustrated in FIGS. 1-9 all have passages through which the suture extends. In the embodiment of the invention illustrated in FIG. 10, the anchor has an eyelet through which the suture extends. Since the embodiment of the invention illustrated in FIG. 10 is generally similar to the embodiment of the invention illustrated in FIGS. 1-9, similar numerals will be utilized to designate similar components, the suffix letter "e" being associated with the embodiment of the invention illustrated in FIG. 10 to avoid confusion.

An anchor 20*e* has a solid cylindrical body portion 116*e*. The body portion 116*e* of the anchor 20*e* is formed of a hydrophilic polymeric material which absorbs body liquid when exposed to the body liquid. The material forming the body portion of the anchor 20*e* is the same as the material forming the anchor 20 of FIGS. 1-4. Upon absorbing body liquid, a portion 116*e* of the anchor 20*e* expands.

In accordance with a feature of the embodiment of the invention illustrated in FIG. 10, the anchor 20*e* is provided with a trailing end portion 160 which is connected with a suture. The trailing end portion 160 of the anchor 20*e* has a circular wall 162 which is fixedly connected with the body portion 116*e* of the anchor 20*e*. A passage 30*e* is formed in a projection 164 which extends axially outward from the end wall 162. The passage 30*e* receives a suture. The suture may be tied off on the projection 164 or may extend through the projection and have a pair of legs, corresponding to the legs 34 and 38 of the suture 32 of FIG. 1.

When the anchor 20*e* is inserted into body tissue, using an inserter assembly similar to the inserter assembly 60 of FIGS. 1 and 2, the body portion 116*e* is exposed to body liquid. This results in the body portion 116*e* of the anchor 20*e* expanding radially and axially outward from the trailing end portion 160 to form a mechanical interlock with the body tissue.

Anchor—Sixth Embodiment

In the embodiments of the invention illustrated in FIGS. 1-10, at least portions of the anchors are formed of a hydrophilic polymeric material which absorbs body liquid. In the embodiment of the invention illustrated in FIG. 11, the anchor is formed of cellular material which absorbs body liquid. Since the embodiment of the invention illustrated in FIG. 11 is generally similar to the embodiments of the invention illustrated in FIGS. 1-10, similar numerals will be utilized to designate similar components, the suffix letter "f" being associated with the numerals of FIG. 11 to avoid confusion.

A suture anchor 20*f* has a tubular cylindrical configuration when the anchor is in an unrestrained condition. When the suture anchor 20*f* is in an unrestrained condition, the anchor has a tubular wall 24*f* which has a cylindrical outer side surface 26*f* which is coaxial with a cylindrical inner side surface 28*f* of the anchor. The cylindrical inner side surface 28*l* forms a passage 30*f* which extends axially through the center of the suture anchor 20*f* when the anchor is in an unrestrained condition.

The wall 24*f* of the suture anchor 20*f* is formed as one piece of resilient material containing a large number of cells which are expandable to absorb body liquid. The cellular material which forms the suture anchor 20*f* may be a hydrophilic polymeric cellular material which absorbs body liquid. Although it is preferred to form the anchor 20*f* with a cylindrical configuration, the anchor may be shaped to any one of many different axially tapering or flaring configurations or may have a polygonal configuration.

A suture 32*f* is inserted into the passage 30*f* in the suture anchor 20*f*. The suture 32*f* includes a leg portion 34*f* which extends away from a flat annular trailing end surface 36*f* of the anchor 20*f*. In addition, the suture 32*f* has a second portion or leg 38*f* which extends across a flat annular leading end surface 40*f* of the anchor 20*f*. The leg 38*f* of the suture 32*f* extends along the cylindrical outer side surface 26*f*. A relatively short portion 44*f* of the suture 32*f* interconnects the leg portion 34*f* and 38*f* and is disposed in the passage 30*f* in the anchor 20*f*.

An inserter assembly 60*f* is used to position the anchor 20*f* and a portion of the suture 32*f* in a patient's body tissue 22*f*. The inserter assembly 60*f* includes a cylindrical tubular outer sleeve 66*f* having a cylindrical passage 68*f* in which the anchor 20*f* is disposed. The inserter 60*f* also includes a cylindrical tubular inner sleeve 72*f* which is telescopically received in the outer sleeve 66*f*. The tubular inner sleeve 72*f* has a cylindrical leading end portion 74*f* which engages the trailing end surface 36*f* of the anchor 20*f*.

The leading end portion 74*f* of the tubular inner sleeve 72*f* has an end wall 168 with a flat end surface which abuttingly engages the flat annular trailing end surface 36*f* on the anchor 20*f*. The two legs 34*f* and 36*f* of the suture 32*f* extend through a central opening formed in the end wall 168 at the leading end portion 74*f* of the inner sleeve 72*f*. The legs 34*f* and 38*f* of the suture 32*f* extend through the tubular inner sleeve 72*f* to a location remote from the inserter assembly 60*f*. If desired, one of the legs 34*f* or 38*f* of the suture could be omitted. If this was done, the suture 32*f* could be tied or otherwise secured to the anchor 20*f*.

It is contemplated that the anchor 20*f* may be inserted into a human patient's body at many different locations. The anchor 20*f* may be inserted into either hard or soft tissue. In the situation illustrated schematically in FIG. 11, the anchor 20*f* is being inserted into soft body tissue in a patient's body.

To facilitate insertion of the anchor 20*f* into soft body tissue, a leading end portion 170 of the outer sleeve 60*f* has an axially tapered or pointed configuration. The pointed configuration of the leading end portion 170 of the outer sleeve 601 enables the leading end portion of the outer sleeve to form an opening in an imperforate outer side surface 114*f* of the patient's body tissue 22*f*. In addition, the pointed leading end portion 170 of the outer sleeve 60*f* facilitates moving the outer sleeve 60*f* into the body tissue 22*f* under the influence of force manually applied against an outer end portion of the outer sleeve 60*f*.

To insert the anchor 20*f* into the patient's body tissue 22*f*, the pointed leading end portion 170 of the outer sleeve 66*f* is pressed against the imperforate outer side surface 114*f* of skin or other tissue 120*f*. The pointed leading end portion of the outer sleeve 661 pierces the imperforate outer surface 114*f* of the skin 120*f* and enters soft body tissue 122*f* disposed beneath the skin. The outer sleeve 66*f* is forced into the soft body tissue 22*f* for a desired distance corresponding to the distance which the suture anchor 20*f* is to be inserted into the body tissue.

The inner sleeve 72*f* is then pressed downward (as viewed in FIG. 11) to move the suture anchor 20*f* to the leading end portion 170 of the outer tubular member 66*f*. The inner side surface 68*f* of the tubular outer member 66*f* applies force against the outer side surface 26*f* of the anchor 20*f* to maintain the anchor in the compressed condition shown in FIG. 11. The outer tubular member 66*f* is then moved axially upward (as viewed in FIG. 11) relative to the stationary inner tubular member 72*f*. This results in the anchor 20*f* being ejected from the outer tubular member 66*f* into the body tissue 22*f*. Once the anchor 20*f* has moved from the outer sleeve 66*f* into the body tissue 22*f*, both the inner and outer sleeves 66*f* and 72*f* are withdrawn from the body tissue.

If desired, a pointed member, such as a trocar, could be inserted through the outer sleeve 66*f* to pierce the surface 114*f* and body tissue 22*f*. If this was done, the inner sleeve 72*f* and anchor 20*f* would be removed from the outer sleeve 66*f* to provide room for the pointed member. After the body tissue has been pierced by the pointed member, the pointed member would be withdrawn from the outer sleeve 66*f* and the inner sleeve 72*f* and compressed anchor 20*f* inserted into the outer sleeve.

In accordance with a feature of the present invention, the anchor 20*f* is formed of a resilient cellular material. Prior to insertion of the anchor 20*f* into the outer sleeve 66*f*, the cellular material of the anchor 20*f* is resiliently compressed from a relatively large unrestrained size to a compacted size illustrated in FIG. 11. The unrestrained size of the suture anchor 20*f* may be 2 to 20 times as large as the size illustrated in FIG. 11.

As the resilient cellular material of the anchor 20*f* is compressed, the passage 30*f* which extends through the anchor 20*f* when the anchor is in its unrestrained condition, is collapsed tightly inward against the portion 44*f* of the suture 32*f*. In addition, as the anchor 20*f* is resiliently compressed from its unrestrained condition, the cells in the anchor are collapsed. Thus, the anchor 20*f* is resiliently compressed from an unrestrained condition to the compacted or compressed condition of FIG. 11 in much the same manner as in which a sponge may be compressed.

The compressed anchor 20*f*, with the suture 32*f* extending through the anchor and the inner sleeve 72*f*, is inserted into the outer sleeve 66*f*. The inner sleeve 72*f* then pushes the compressed anchor axially downward (as viewed in FIG. 11) into the outer sleeve as the telescopic relationship between the inner and outer sleeves is increased.

When the anchor 20*f* is in the outer sleeve 66*f*, the inner side surface 68*f* of the outer sleeve applies force against the outer side surface 26*f* of the anchor to hold the anchor in its compressed condition. Upon movement of the anchor 20*f* out of the outer sleeve 66*f* into the body tissue 22*f*, the force holding the anchor 20*f* in a compressed condition is removed from the outer side surface 26*f* of the anchor. As this occurs, the natural resilience of the cellular material forming the anchor 20*f* causes the anchor to expand.

As the anchor 20*f* expands, the anchor applies force against the soft body tissue 122*f* and increases the size of the cavity which was originally formed by the outer sleeve 66*f* of the inserter assembly 60*f*. As the anchor 20*f* expands, it applies force against the soft body tissue 122*f* and displaces the soft body tissue. Thus, the outer side surface 26*f* of the anchor 20*f* is pressed against the soft body tissue 122*f* and moves the soft body tissue as the anchor expands radially outward.

As the anchor 20*f* expands, the cells in the anchor are expanded from a collapsed condition to an expanded condition. As the size of the cells in the anchor 20*f* increases, body liquids are drawn into the cells. Thus, the anchor 20*f* absorbs body liquid as it expands.

The anchor 20*f* is formed of a resilient polymeric material having an open cell, sponge-like construction. When the anchor 20*f* is in the compressed condition illustrated in FIG. 11, the cells are collapsed. As the anchor 20*f* expands in the body tissue 22*f*, the cells expand. Since the anchor 20*f* has an open cellular construction, body liquid can flow into the cells as the anchor expands.

Once the anchor 20*f* has expanded in the body tissue 22*f*, the expanded anchor is substantially larger than the opening which was formed in the body tissue by insertion of the outer sleeve 66*f* into the body tissue. However, it should be understood that due to force applied against the anchor 20*f* by the body tissue 22*f*, the anchor may not expand fully back to its unrestrained size. As the outer sleeve 66*f* is withdrawn from the body tissue, the visco-elastic nature of the body tissue causes the body tissue to come together and close off the passage which was formed by the insertion of the outer sleeve 66*f* into the body tissue. Thus, the body tissue will move inward and grip the legs or portions 34*f* and 38*f* of the suture 32*f*. The anchor 20*f* will fill a cavity formed in the body tissue 22*f* by expansion of the anchor.

The expansion of the anchor 20*f* in the body tissue results in the formation of an interlock between the anchor and the body tissue to prevent the anchor from being pulled out of the body tissue under the influence of tension applied to the suture 32*f*. The suture 32*f* may be used to position a member which is body tissue, in the manner similar to that illustrated in FIGS. 3 and 4, or may be used to position a splint or implant member relative to the body tissue. Since the expanded anchor 20*f* has a firm interlock with the body tissue 122*f*, tension forces transmitted through the suture 32*f* between the anchor 20*f* and a member held in place by the suture will not pull the anchor 20*f* out of the body tissue.

In FIG. 11, the compressed suture anchor 20*f* is being inserted into a solid mass of soft body tissue 122*f*. However, it is contemplated that the suture anchor 20*f* could be inserted into either a natural or artificial body cavity. If this was done the suture anchor 20*f* would expand to at least partially fill the body cavity.

Alternative Anchor Insertion Apparatus

Figure 12:
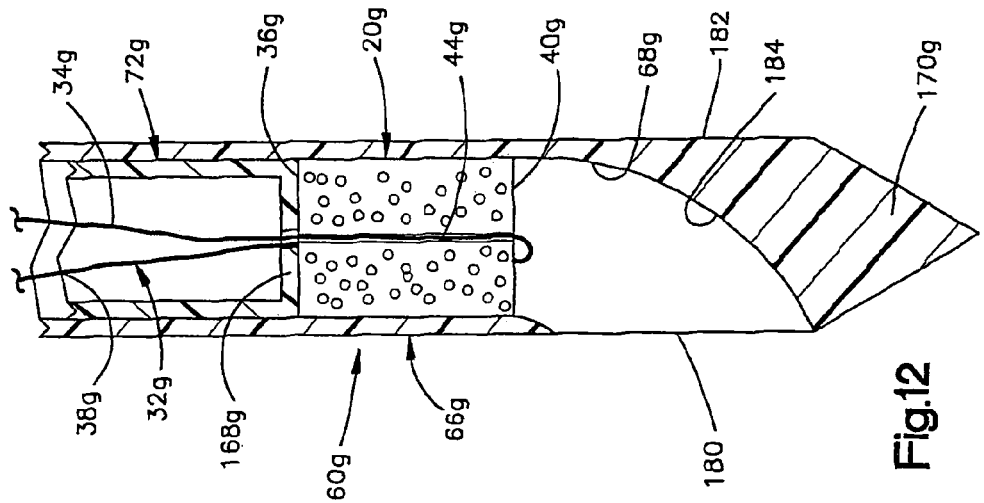
FIG. 12 is a schematic illustration of another apparatus for inserting the anchor of FIG. 11 into body tissue.

In the embodiment of the invention illustrated in FIG. 11, the anchor 20*f* moves through the open end portion 170 of the outer sleeve 66*f* into the body tissue 22*f*. In the embodiment of the invention illustrated in FIG. 12, the outer sleeve has a closed pointed end portion and the anchor is moved from the outer sleeve at a location immediately behind the pointed end portion of the outer sleeve. Since the embodiment of the invention illustrated in FIG. 12 is generally similar to the embodiment of the invention illustrated in FIG. 11 similar numerals will be utilized to designate similar components, the suffix letter "g" being associated with the numerals of FIG. 12 to avoid confusion.

An anchor 20*g* has the same construction and is formed of the same resilient open cell material as the anchor 20*f* of FIG. 11. A suture 32*g* has a leg or portion 34*g* which extends from a flat annular trailing end surface 36*g* of the cylindrical anchor 20*g*. A second leg or portion 38*g* of the suture 32*g* extends from a flat annular leading end surface 40*g* of the anchor 20*g*. A portion 44*g* of the suture 32*g* extends through the anchor and interconnects the legs or portions 34*g* and 38*g*.

The two legs or portions 34*g* and 38*g* of the suture 32*g* extend through a cylindrical central passage in an outer sleeve 72*g* of an inserter assembly 60*g*. The inner sleeve 72*g* is disposed in a telescopic relationship with a cylindrical outer sleeve 66*g* of the inserter assembly 60*g*. The inner sleeve 72*g* cooperates with the outer sleeve 66*g* in the same manner as previously explained in conjunction with the inserter assembly of FIG. 11.

In accordance with a feature of this embodiment of the invention, the outer sleeve 66*g* has a solid pointed end portion 170*g* with a generally conical configuration. The pointed end portion 170*g* is utilized to pierce an imperforate surface of body tissue in much the same manner as in which the end portion 170 of the outer sleeve 66*f* of the inserter assembly 60*f* (FIG. 11) is used to pierce an imperforate surface 114*f* of the body tissue 22*f*.

In accordance with one of the features of the present invention, the outer sleeve 66*g* has a generally oval opening 180 in a cylindrical outer side surface 182 of the outer sleeve 66*g*. The opening 180 is connected with a central passage 68*g*. The passage 68*g* extends from an open upper (as viewed in FIG. 12) end portion of the outer sleeve 66*g* to the solid pointed leading end portion 170*g*.

When the outer sleeve 66*g* has been inserted to the desired depth in body tissue, the inner sleeve 72*g* is moved axially downward (as viewed in FIG. 12) and the anchor 20*g* is forced along an arcuate cam surface 184 leading to the opening 180. This results in the anchor 20*g* being forced from the passage 68*g* in the outer sleeve 66*g* into the soft body tissue. As this occurs, the leading end 40*g* of the anchor 20*g* applies force against the body tissue to displace the body tissue and provide space for the anchor.

As the anchor 20*g* moves along the passage 68*g* and through the opening 180, the orientation of the anchor relative to the body tissue changes. Thus, the orientation of the anchor 20*g* changes from the orientation shown in FIG. 12 to an orientation similar to the orientation of the anchor 20 in FIG. 3. This pivotal movement of the anchor 20*g* results in the anchor moving from an initial orientation in which a central axis of the anchor extends parallel to and is coincident with a central axis of the outer sleeve 66*g* to an orientation in which the central axis of the anchor 20*g* extends perpendicular to the central axis of the outer sleeve 66*g*.

As the anchor 20*g* exits from the passage 68*g* in the outer sleeve 66*g*, the anchor 20*g* expands under the influence of its own natural resilience and further displaces body tissue. Once the inner sleeve 72*g* has been moved downward to the maximum extent possible, that is, to a position in which the leading end of the inner sleeve 72*g* engages the cam surface 184, the inner and outer sleeves are withdrawn together from the body tissue. As this occurs, engagement of the anchor 20*g* with the body tissue causes the trailing end portion of the anchor to move out of the passage 68*g* in the outer sleeve 66*g*.

As the outer sleeve 66*g* continues to be withdrawn, the pointed leading portion 170 of the outer sleeve moves upward (as viewed in FIG. 12), past the anchor 20*g*. As this occurs, the anchor 20*g* expands into the space previously occupied by the leading end portion 170*g* of the outer sleeve 66*g*. As the outer sleeve 66*g* and inner sleeve 72*g* are withdrawn from the body tissue, the visco-elastic body tissue closes around the anchor 20*g* and the legs 34*g* and 38*g* of the suture 32*g*.

As the anchor 20*g* is forced from the outer sleeve 66*g* into the body tissue and expands, cells in the anchor 20*g* also expand. As the cells in the anchor 20*g* expand, body liquid is drawn into and at least partially fills the cells in the anchor. The anchor 20*g* has an open cellular construction, similar to the construction of a sponge. The anchor 20*g* is resiliently compressed prior to insertion into the outer sleeve 66*g* so that the cells in the anchor 20*g* are resiliently collapsed until the anchor is allowed to expand as it is forced out of the side opening 180 in the outer sleeve 66*g*.

Changing Configuration of Anchor

Figure 13:
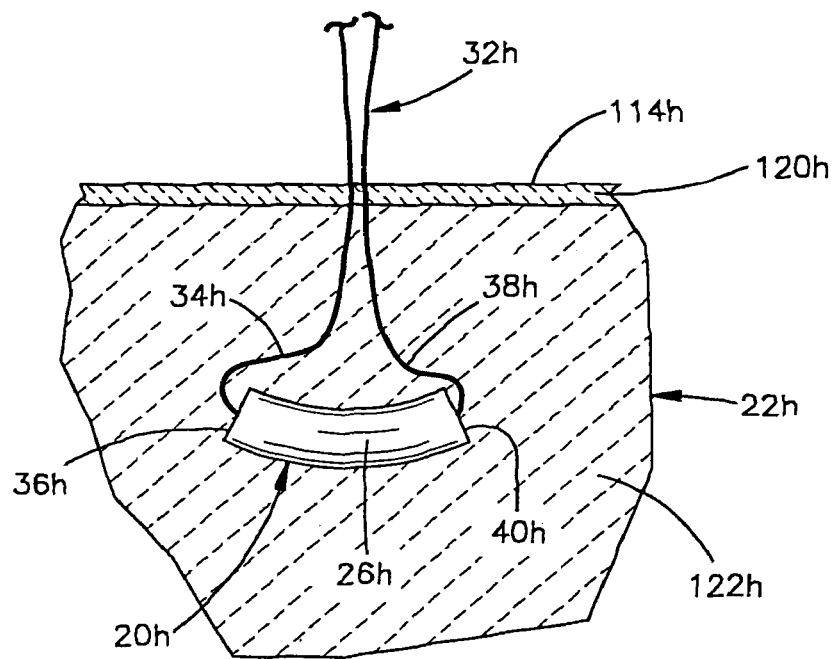
FIG. 13 is a schematic illustration of the manner in which the configuration of an anchor is changed while the anchor is in the patient's body tissue.

In the embodiment of the invention illustrated in FIGS. 1-3, the general configuration of the anchor 20 is illustrated as being maintained constant. Thus, the anchor 20 has a cylindrical tubular configuration with a linear central axis. In the embodiment of the invention illustrated in FIG. 13, the configuration of the anchor is changed while the anchor is in a patient's body tissue. Since the embodiment of the invention illustrated in FIG. 13 is generally similar to the embodiment of the invention illustrated in FIGS. 1-4, similar numerals will be utilized to designate similar components, the suffix letter "h" being associated with the numerals of FIG. 13 to avoid confusion.

A suture anchor 20*h* has the same construction and is formed of the same hydrophilic polymeric material as the suture anchor 20 of FIGS. 1-3. The suture anchor 20*h* (FIG. 13) has a cylindrical tubular configuration. The suture anchor 20*h* has a cylindrical outer side surface 26*h*. A cylindrical central passage (not shown) extends through the suture anchor 20*h* between opposite annular end surfaces 36*h* and 40*h* of the suture anchor 20*h*.

A suture 32*h* has a leg 34*h* which extends from an annular end surface 36*h* of the anchor 20*h*. A second leg 38*h* of the suture 32*h* extends from the opposite end surface 40*h* of the anchor 20*h*. The anchor 20*h* is inserted into body tissue 20*h* in the same manner as in which the anchor 20*f* of FIG. 11 is inserted into the body tissue 22*f*. Thus, an inserter assembly, similar to the inserter assembly 60*f* of FIG. 11, is used to position the anchor 20*h* in the body tissue 22*h*. The inserter assembly may include a tubular outer sleeve, corresponding to the sleeve 66*f* of FIG. 11 and a tubular inner sleeve, corresponding to the inner sleeve 72*f* of FIG. 11. However, the inner sleeve 72*f* is provided with a conical leading end portion having a configuration corresponding to the configuration of the leading end portion 74 (FIG. 1) of the inner sleeve 72. This enables the inserter assembly to pivot the suture anchor 20*h* to the position shown in FIG. 13.

The outer sleeve of the inserter assembly which is used to position the anchor 20*h* in the body tissue 22*h* has a pointed leading end portion, corresponding to the pointed leading end 170 of the outer sleeve 66f of the inserter assembly 60f of FIG. 11. The pointed leading end of the outer sleeve of the inserter assembly was used to pierce the imperforate outer side surface 114h of skin 120h and to enter soft body tissue 122h.

As the anchor 20h was positioned in the soft body tissue 122h, the opposite legs 34h and 38h of the suture 32h were tensioned. This resulted in the suture 32h applying force against the opposite flat annular end surfaces 36h and 40h of the anchor 20h. The force applied to opposite ends of the anchor 20h by the suture 32h pulled the outer side surface 26h of the anchor against the body tissue 122h. In addition, the force applied against opposite ends of the anchor 20h by the suture 32h caused the suture to bend from an initial configuration to the deflected configuration shown in FIG. 13.

When the anchor 20h was in the initial configuration, the anchor 20h had a straight longitudinal central axis, the same as the anchor 20 of FIGS. 1-3. However, tensioning the suture 32h caused the legs 34h and 38h of the suture to apply force against opposite ends of the anchor 20h and pull the anchor against the body tissue 122h. As this occurred, the anchor was deflected to the arcuate configuration illustrated in FIG. 13. Since the anchor 20h is formed of the same hydrophilic polymeric material as the anchor 20 of FIGS. 1-3, the anchor 20h absorbs body fluid and expands in the body tissue 122h while the anchor has the deflected configuration illustrated in FIG. 13.

Deflection of Anchor—Second Embodiment

Figure 14:
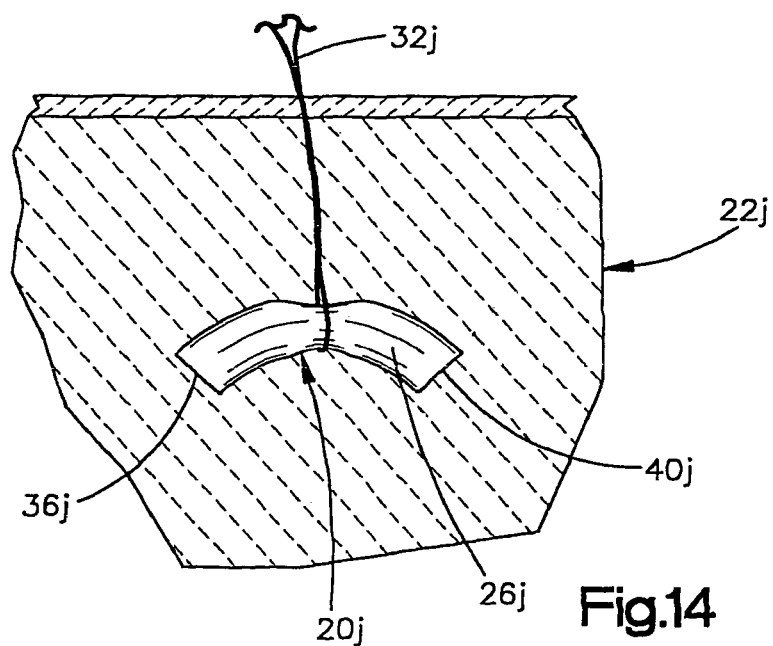
FIG. 14 is a schematic illustration of another manner in which the configuration of an anchor is changed while the anchor is in a patient's body tissue.

In the embodiment of the invention illustrated in FIG. 13, the configuration of the anchor 20h is changed from an initial configuration in which the anchor has a straight longitudinal central axis to a configuration in which the anchor has an arcuate longitudinal central axis by tensioning the suture 32h to apply force against opposite ends of the anchor. In the embodiment of the invention illustrated in FIG. 14, the configuration of the anchor is changed from an initial configuration to a deflected configuration by tensioning a suture which is connected with a central portion of the anchor. Since the embodiment of the invention illustrated in FIG. 14 is generally similar to the embodiment of the invention illustrated in FIG. 13, similar numerals will be utilized to designate similar components, the suffix letter "j" being associated with the numerals of FIG. 14 to avoid confusion.

An anchor 20j has an outer side surface 26j. The outer side surface 26j extends between opposite end surfaces 36j and 40j of the anchor.

A suture 32j is connected with a central portion of the anchor 20j disposed between the opposite end surfaces 36j and 40j. The anchor 20j is formed of the same hydrophilic polymeric material as the anchor 20 of FIGS. 1-3. The anchor 20j is inserted into body tissue 22j in the same manner as described in connection with the embodiment of the invention illustrated FIG. 13.

Prior to insertion of the anchor 20j into the body tissue 22j, the anchor 20j has a solid cylindrical configuration with a straight longitudinal central axis. As the anchor 20j is inserted into the body tissue 22j and moved to the orientation shown in FIG. 14, the suture 32j is tensioned. Tensioning of the suture 32j presses the outer side surface 26j of the anchor 20j against the body tissue 22j. As this occurs, the anchor 20j is deflected from its initial configuration to the deflected configuration illustrated in FIG. 14. When the anchor 20j is in the deflected orientation, the longitudinal central axis of the anchor has an arcuate configuration.

What is claimed is:

1. An anchor for securing a suture relative to bone comprising:
a generally cylindrical body portion having an exterior surface, a leading end configured to facilitate insertion of the body portion into the bone, a trailing end opposite the leading end, and a generally cylindrical opening extending from the trailing end toward the leading end, the generally cylindrical opening having a central axis, the body portion having a length and a central longitudinal axis extending from the leading end to the trailing end, the generally cylindrical opening having a length that is greater than a majority of the length of the body portion, the central axis of the generally cylindrical opening being coaxial with the central longitudinal axis of the body portion;
a passage located proximate the leading end of the body portion for receipt of the suture, the passage having a central axis, the central axis of the passage being oriented transverse to and intersecting both the central longitudinal axis of the body portion and the central axis of the generally cylindrical opening, the anchor being formed of at least two different materials suitable for implantation in bone, a first of the at least two different materials forming a perimeter around the generally cylindrical opening, a second of the at least two different materials forming the leading end; and
bone engaging projections configured to secure the anchor in the bone,
wherein the anchor is structured to permit the suture to be positioned along a majority of the length of the exterior surface of the body portion to secure the suture between the bone and the anchor when the anchor is implanted in the bone.

2. The anchor of claim 1, wherein the trailing end includes a generally flat annular surface transverse to the central longitudinal axis of the body portion.

3. The anchor of claim 1, wherein a cross-section of the suture passage has an uninterrupted perimeter.

4. The anchor of claim 1, wherein the opening is configured to permit at least a portion of a suture to be disposed therein.

5. The anchor of claim 1, wherein the leading end of the body portion is at least in part conical.

6. The anchor of claim 1, further comprising a pointed tip to facilitate piercing the bone.

7. The anchor of claim 1, wherein at least one of the at least two different materials is a polymeric material.

8. The anchor of claim 7, wherein the polymeric material is a copolymer.

9. The anchor of claim 7, wherein the polymeric material is a dipolymer.

10. The anchor of claim 7, wherein the polymeric material is one selected from the group consisting of cellulose, petroglutamic acid, high purity carboxymethylcellulose, a collagen, and a polylactide.

11. The anchor of claim 1, wherein the trailing end is configured to be engaged by a driver.

12. The anchor of claim 1, wherein the body portion is implantable in soft tissue.

13. The anchor of claim 1, wherein the bone engaging projections comprise ribs projecting radially from the exterior surface of the cylindrical body portion.

* * * * *